United States Patent
Audière et al.

(10) Patent No.: US 11,850,098 B2
(45) Date of Patent: Dec. 26, 2023

(54) METHOD AND DEVICE FOR MEASURING AN ULTRASOUND PARAMETER OF A VISCOELASTIC MEDIUM

(71) Applicant: ECHOSENS, Paris (FR)

(72) Inventors: Stéphane Audière, Paris (FR); Laurent Sandrin, Bourg-la-Reine (FR)

(73) Assignee: ECHOSENS, Paris (FR)

( * ) Notice: Subject to any disclaimer, the term of this patent is extended or adjusted under 35 U.S.C. 154(b) by 331 days.

(21) Appl. No.: 16/441,970

(22) Filed: Jun. 14, 2019

(65) Prior Publication Data
US 2020/0390421 A1  Dec. 17, 2020

(51) Int. Cl.
*A61B 8/08* (2006.01)
*A61B 8/14* (2006.01)

(52) U.S. Cl.
CPC .......... *A61B 8/485* (2013.01); *A61B 8/14* (2013.01); *A61B 8/5246* (2013.01)

(58) Field of Classification Search
CPC ......... A61B 8/485; A61B 8/5246; A61B 8/14; A61B 8/085; A61B 8/5207; A61B 8/5223; A61B 8/08; A61N 7/00
See application file for complete search history.

(56) References Cited

U.S. PATENT DOCUMENTS

| | | | | |
|---|---|---|---|---|
| 2012/0016237 A1* | 1/2012 | Tanigawa | ............ | G01S 7/52034 600/438 |
| 2012/0083692 A1* | 4/2012 | Stoll | ............ | A61B 8/429 600/437 |
| 2012/0190938 A1* | 7/2012 | Addington | ............ | A61B 5/4238 600/301 |
| 2012/0190983 A1* | 7/2012 | Sandrin | ............ | A61B 8/485 600/442 |
| 2014/0249415 A1* | 9/2014 | Sandrin | ............ | A61B 8/5223 600/442 |
| 2015/0190117 A1 | 7/2015 | Arai et al. | | |

(Continued)

FOREIGN PATENT DOCUMENTS

| CN | 102151152 A | 8/2011 |
|---|---|---|
| CN | 104363836 A | 2/2015 |

(Continued)

OTHER PUBLICATIONS

Sasso et al.: Liver Steatosis Assessed by Controlled Parameter (CAP) Measured with the XL Probe of the FibroScan: a Pilot Study Assessing Diagnostic Accuracy, vol. 42 No. 1, Jan. 2016, p. 92-103 (Year: 2016).*

(Continued)

*Primary Examiner* — Boniface Ngathi

(74) *Attorney, Agent, or Firm* — Pillsbury Winthrop Shaw Pittman LLP

(57) ABSTRACT

A system and method for accumulating ultrasound attenuation data for the detection of disease or other conditions. In one embodiment, an ultrasound system generates a number of imaging pulses during an imaging mode. Echo signals received from the imaging pulses are tested against one or more quality metrics. Attenuation data from the echo signals that pass the quality metrics are accumulated and are used to compute a tissue characteristic. In one embodiment the tissue characteristic is a CAP measurement that is related to an amount of fat in a liver.

18 Claims, 13 Drawing Sheets

(56) References Cited

U.S. PATENT DOCUMENTS

| | | | |
|---|---|---|---|
| 2015/0216507 A1* | 8/2015 | Greenleaf | G01N 29/262 600/438 |
| 2017/0258438 A1* | 9/2017 | Kanayama | A61B 8/463 |
| 2017/0322308 A1* | 11/2017 | Loupas | G01S 7/52022 |
| 2019/0076128 A1 | 3/2019 | Hah | |
| 2019/0254634 A1* | 8/2019 | Honjo | G01S 7/52073 |

FOREIGN PATENT DOCUMENTS

| | | | |
|---|---|---|---|
| CN | 105266851 A | 1/2016 | |
| CN | 107616809 A | 1/2018 | |
| CN | 107647881 A | 2/2018 | |
| CN | 108652661 A | 10/2018 | |
| FR | 2 949 965 A1 | 3/2011 | |
| FR | 2 978 657 A1 | 2/2013 | |
| JP | 2008-206779 A | 9/2008 | |
| WO | WO-2018019791 A1 * | 2/2018 | A61B 8/08 |
| WO | WO-2019131811 A1 * | 7/2019 | A61B 5/055 |

OTHER PUBLICATIONS

Ferraioli et al.: Liver Ultrasound Elastography: an Update to the World Federation for Ultrasound in Medicine and Biology Guidelines and Recommendations, vol. 44 No. 22, Dec. 2018, p. 2419-2440 (Year: 2018).*

Evans, A., et al. (2010). Quantitative shear wave ultrasound elastography: initial experience in solid breast masses. Breast cancer research : BCR, 12(6), R104. (Year: 2010).*

Bavu, E., et al. (2011). Noninvasive in vivo liver fibrosis evaluation using supersonic shear imaging: a clinical study on 113 hepatitis C virus patients. Ultrasound in medicine & biology, 37(9), 1361-1373. (Year: 2011).*

Athanasiou, A., et al. (2010). Breast lesions: quantitative elastography with supersonic shear imaging—preliminary results. Radiology, 256(1), 297-303. (Year: 2010).*

Evans et al. Quantitative shear wave ultrasound elastography: initial experience in solid breast masses, Breast cancer research : BCR, 12(6), R104, 2010, pp. 1-8 (Year: 2010).*

Sasso et al.: Liver Steatosis Assessed by Controlled Parameter (CAP) Measured with the XL Probe of the FibroScan: a Pilot Study Assessing Diagnostic Accuracy, vol. 42 No. 1, Jan. 2016, pp. 92-103 (Year: 2016).*

Sasso, M., et al., "Controlled Attenuation Parameter (CAP): a Novel VCTE™ Guided Ultrasonic Attenuation Measurement for the Evaluation of Hepatic Steatosis: Preliminary Study and Validation in a Cohort of Patients With Chronic Liver Disease From Various Causes," Ultrasound in Med. & Biol., vol. 36, No. 11, (2010), pp. 1825-1835.

Sandrin, L., et al. "Transient Elastography: a New Noninvasive Method for Assessment of Hepatic Fibrosis," Ultrasound in Medicine and Biology, vol. 29, No. 12, (2003), pp. 1-8.

Sasso, M., et al. "The controlled attenuation parameter (CAP): a novel tool for the non-invasive evaluation of steatosis using Fibroscan®," Clinics and Research in Hepatology and Gastroenterology (2012) 36, pp. 13-20.

Sasso, M., et al., "Liver Steatosis Assessed by Controlled Attenuation Parameter (CAP) Measured With the XL Probe of the Fibroscan: a Pilot Study Assessing Diagnostic Accuracy," Ultrasound in Med. & Biol., (2015), pp. 1-12.

European Search Report as issued in European Patent Application No. 19305761.9, dated Nov. 25, 2019.

Mikolasevic, I., et al., "Transient elastography (FibroScan®) with controlled attenuation parameter in the assessment of liver steatosis and fibrosis in patients with nonalcoholic fatty liver disease—Where do we stand?" World Journal of Gastroenterology, vol. 22, No. 32, (2016), XP055365059, pp. 7236-7251.

Office Action as issued in Chinese Patent Application No. 202010543160.6, dated Sep. 23, 2023.

* cited by examiner

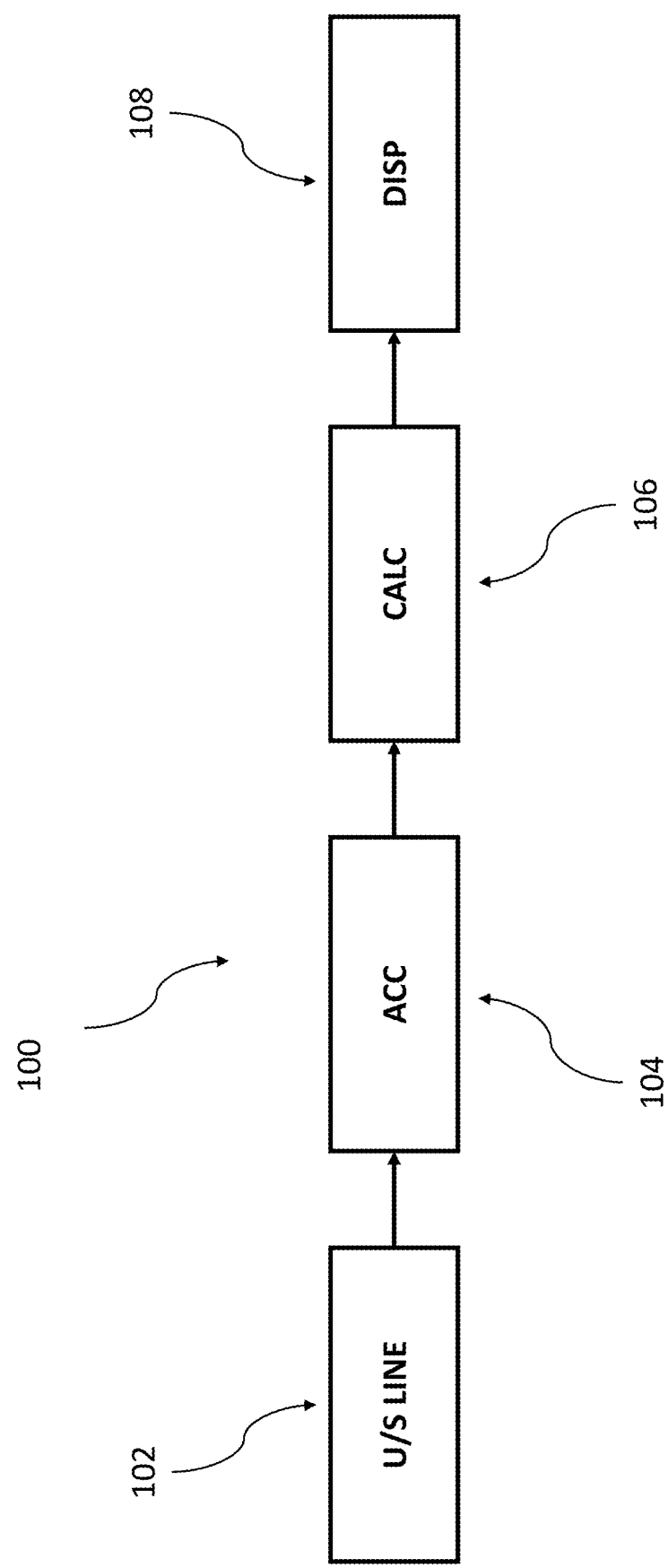

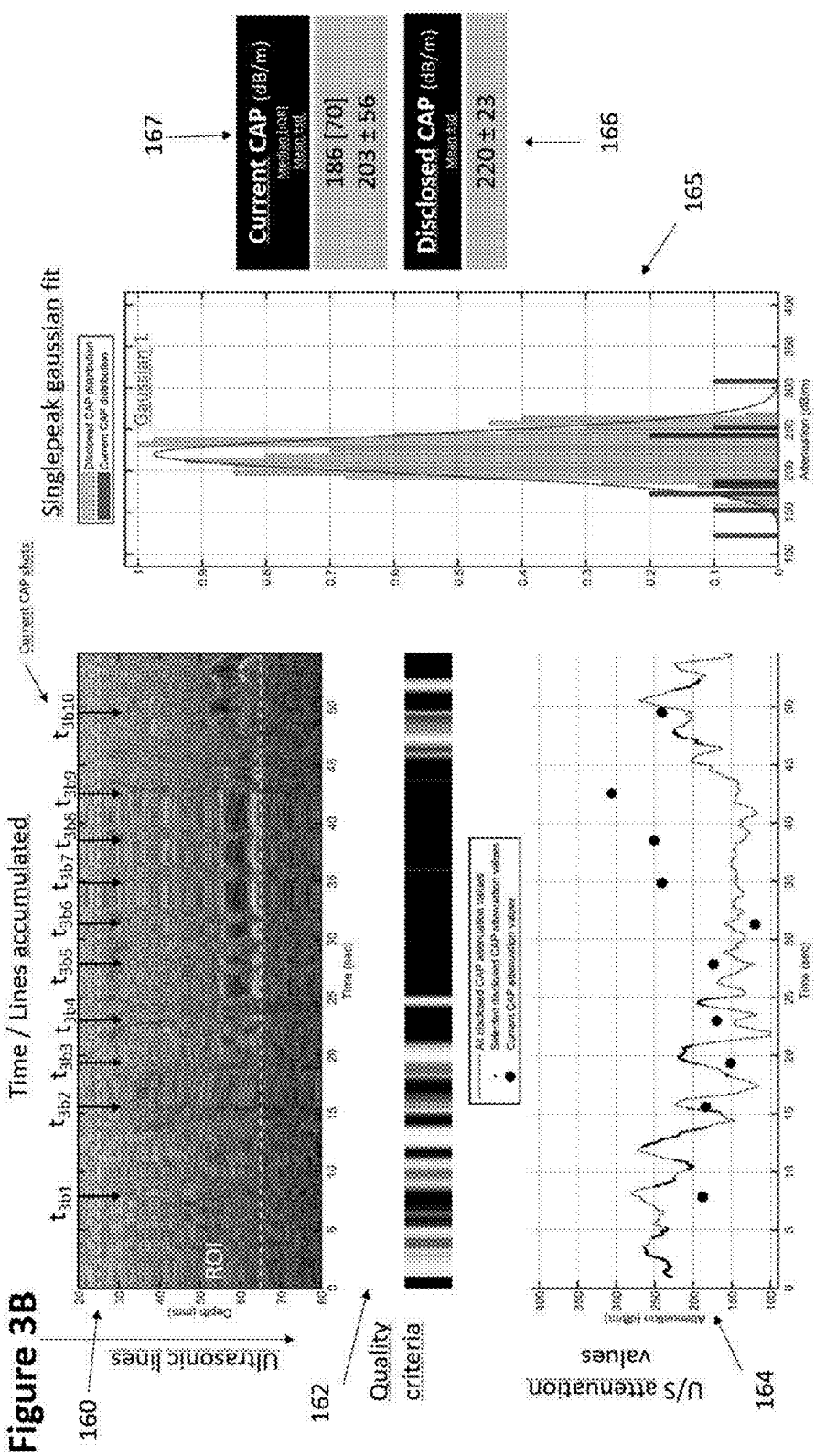

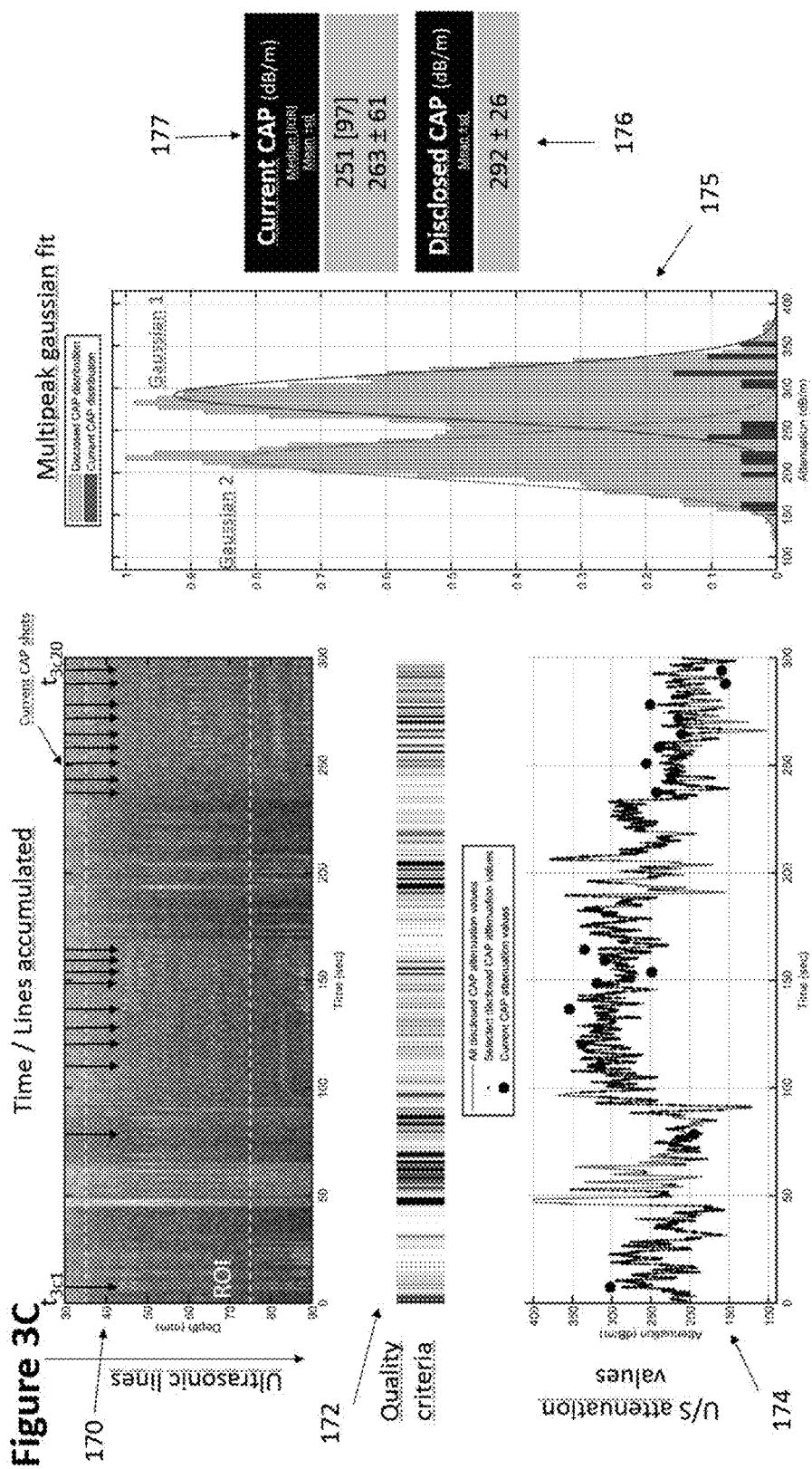

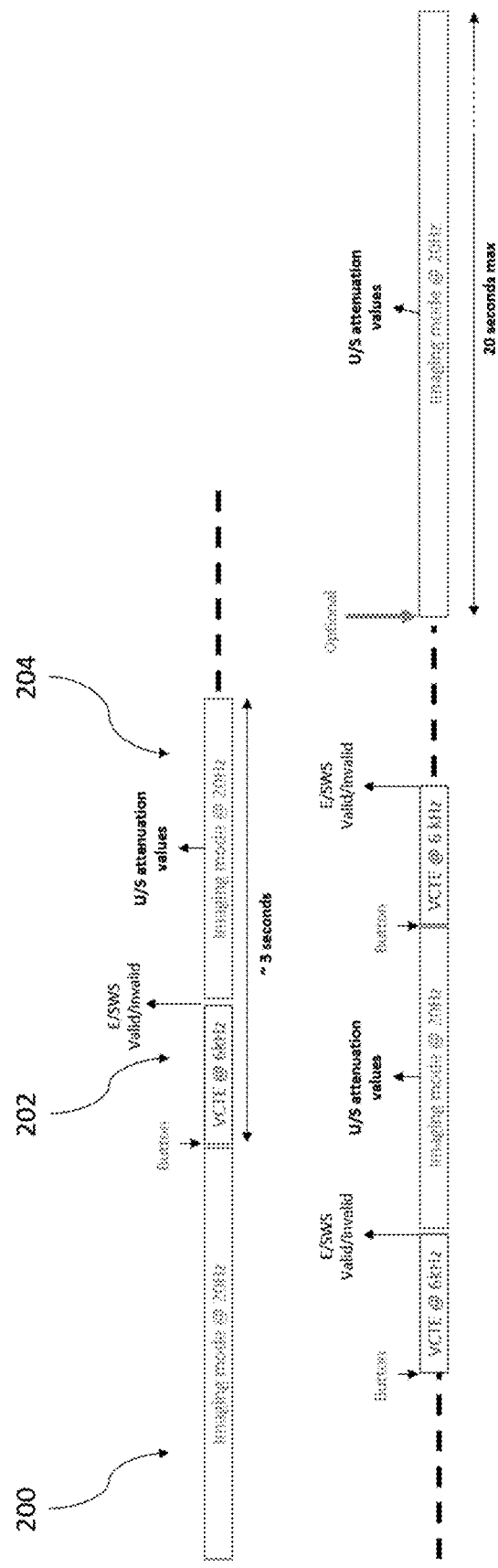

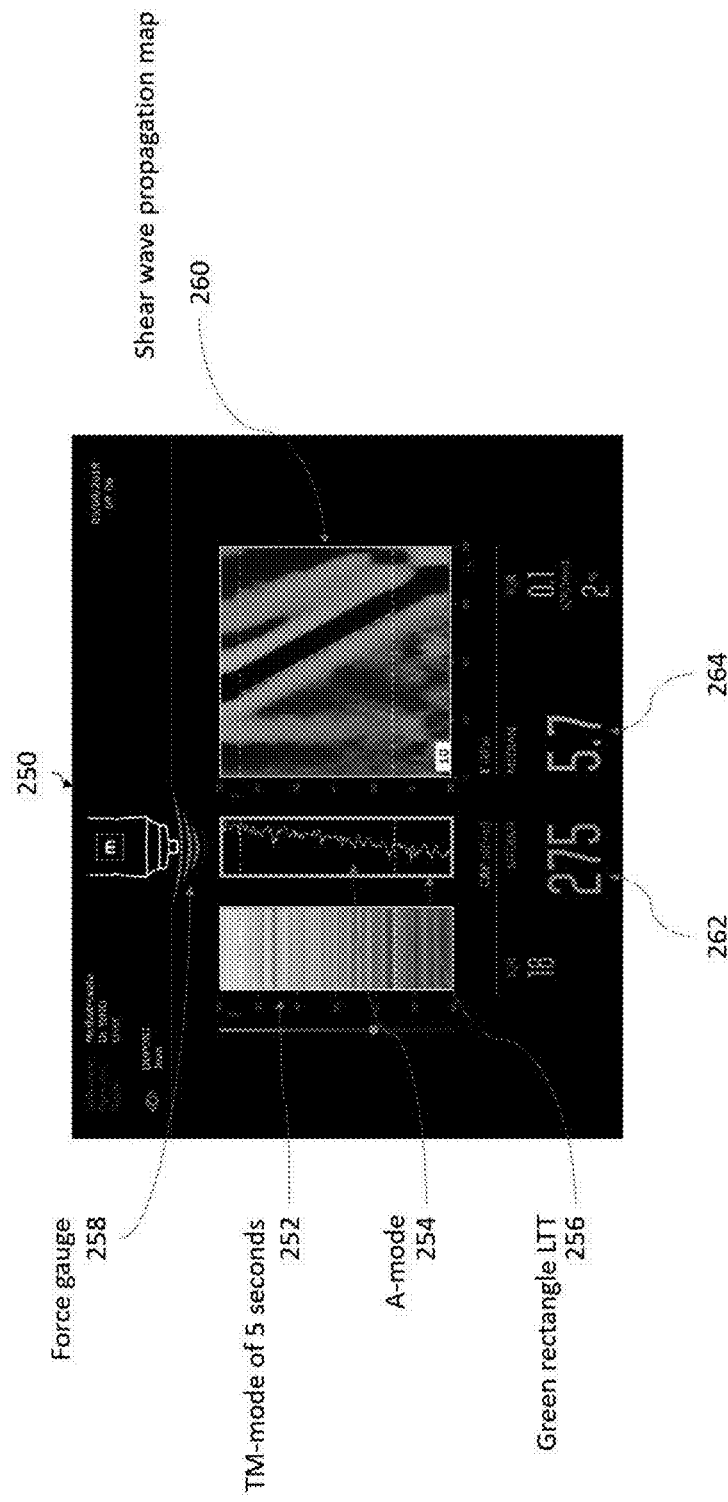

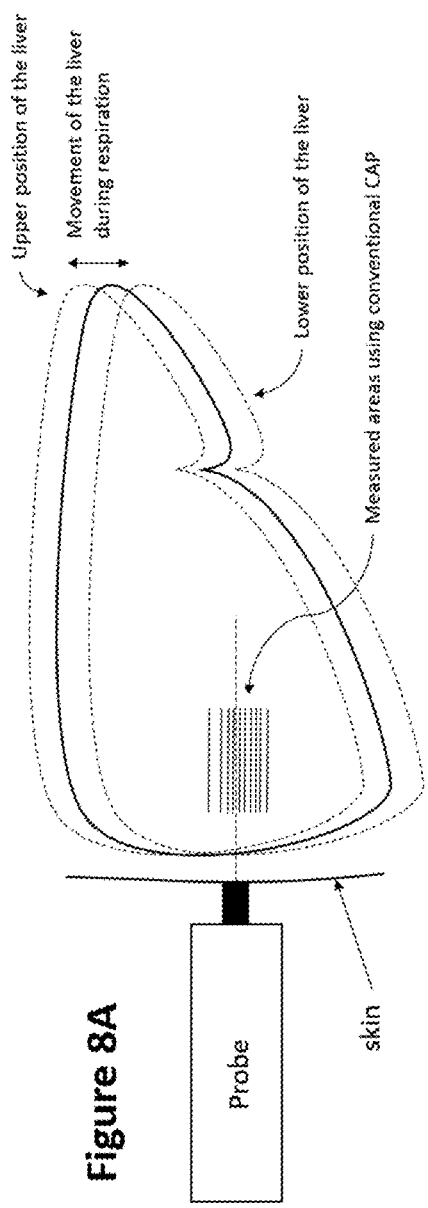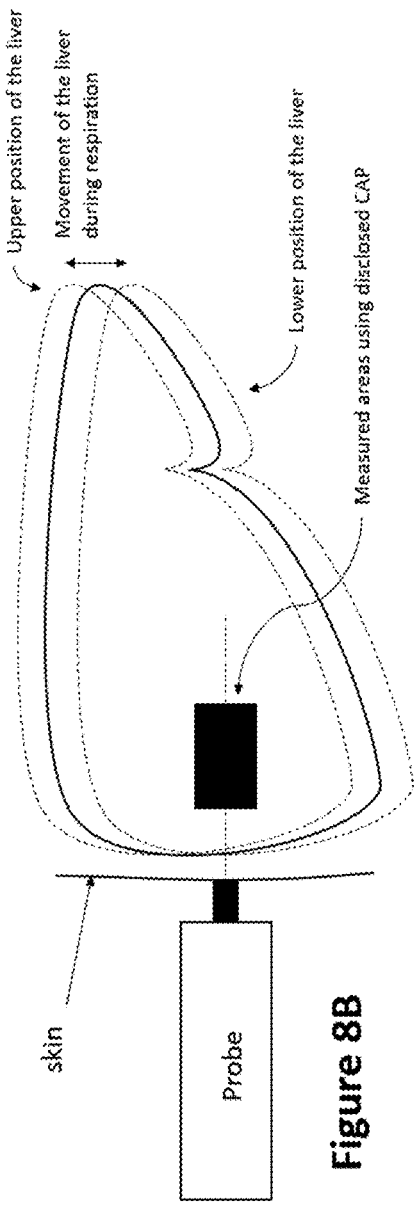

METHOD AND DEVICE FOR MEASURING AN ULTRASOUND PARAMETER OF A VISCOELASTIC MEDIUM

TECHNICAL FIELD

The disclosed technology relates to ultrasound systems and in particular, to systems and methods for measuring ultrasound attenuation in human or animal body tissues to detect liver steatosis and other medical conditions.

BACKGROUND

Due to its ease of use and non-ionizing properties, ultrasound is a commonly used tool for imaging the internal body tissues of human and animal subjects. Ultrasound can also be used to quantify tissue characteristics to detect disease and other medical conditions. One such example is the use of ultrasound in combination with shear waves to measure tissue stiffness in order to detect possible liver disease. Echosens SA of Paris, France (the assignee of the present application) has pioneered the use ultrasound to quantify tissue stiffness by measuring the speed of mechanically induced shear waves that are transmitted through the tissue. Another condition that can be detected with ultrasound is the amount of fat in the liver. It is well known that the amount of fat in the liver changes how ultrasound signals are attenuated as the signals pass through the tissue. Measurements of the ultrasound attenuation (also referred to as a controlled attenuation parameter or "CAP") are therefore a predictor of fatty liver diseases such as liver steatosis.

Echosens currently produces a system for the non-invasive measurement of CAP in a subject that uses the same probe used for Vibration Controlled Transient Elastography or "VCTE" that measures tissue stiffness. For VCTE, the probe applies mechanical vibration to the subject in order to induce a shear wave that travels through the tissue. Ultrasound is then used to track the displacements induced by the propagation of the shear wave and afterwards measure the speed of the shear wave, which is related to the stiffness of the tissue. To measure CAP, the attenuation of the ultrasound signals that are used to track the speed of the shear waves is measured. A CAP measurement is considered valid when the stiffness measurement is considered valid. A detailed explanation of how such VCTE and CAP measurements are obtained can be found in the following papers: "Transient Elastography: a new noninvasive method for assessment of hepatic fibrosis" by L. Sandrin et al., published in Ultrasound in Medicine and Biology, Vol. 29, pages 1705-1713, 2003; "The controlled attenuation parameter (CAP): A novel tool for the non-invasive evaluation of steatosis using Fibroscan®" by M. Sasso et al., published in Clinical Research in Hepatology and Gastroenterology, 2012; "Controlled Attenuation Parameter (CAP): A Novel VCTE™ Guided Ultrasonic Attenuation Measurement for the Evaluation of Hepatic Steatosis: Preliminary Study and Validation in a Cohort of Patients with Chronic Liver Disease from Various Causes" by M. Sasso et al., published in Ultrasound in Medicine and Biology, 2010; and "Liver steatosis assessed by controlled attenuation parameter (cap) measured with the xl probe of the Fibroscan: a pilot study assessing diagnostic accuracy" by M. Sasso et al. published in Ultrasound in Medicine and Biology, 2015, which are herein incorporated by reference.

While the CAP measured according to existing methods shows a good performance statistically in term of area under the ROC curve (over 80% for the diagnosis of the steatosis grade), the CAP value is subject to high variability. For example, in a single patient, the measured CAP value may vary typically around 40 dB/m on a range from 100 to 400 dB/m, which impairs its applicability in a clinical setting, especially for monitoring the disease progression or regression of a patient.

Furthermore, the results are dependent on tissue homogeneity (i.e. no vessels or other tissue structures in the field of view) and can vary based on operator skill. Therefore, there is a need for an improved system for more accurately measuring CAP in subjects.

SUMMARY

To resolve at least partially the problems of the state of the art, the disclosed technology is a system and method for measuring an ultrasound parameter, which is based on recording and automatic analysis of a high number of ultrasonic backscatter signals (e.g. echo signals) acquired during a long period of time (at least 2 second, for example at least 5 seconds, typically 20 seconds) to improve spatial averaging that are validated before being used to calculate the ultrasound parameter.

In contrast with prior art methods in which CAP measurements are carried out during stiffness (VCTE) measurements, an embodiment of the disclosed technology carries out CAP measurements using data or echo signals collected during imaging of the patient's organ (e.g. liver), as opposed to solely during stiffness measurements of the organ. While measuring CAP during stiffness measurements has been thought to be beneficial and reliable because the same collected data or echo signals from the same location on the liver are used to carry out both CAP and stiffness measurements (and thus one could say that steatosis and fibrosis measurements were done at the same location on the patient's liver), the inventors have found that, on the contrary, it was greatly beneficial to measure CAP and stiffness separately because these two parameters require different considerations to make a proper measurement. For example, conventional stiffness measurements require a high frame rate (about 6000 Hz) during a short period of time (about 80 ms) in order to be able to track the shear wave and perform stiffness measurements. By contrast, it was found that CAP measurements should be acquired over a long period of time to increase spatial averaging between the acquired ultrasonic lines and reduce variability of the CAP value. These different considerations for making CAP and stiffness measurements are not sufficiently taken into account when the CAP value is measured at the same time as stiffness. Indeed, during a single stiffness measurement, ultrasound lines or echo signals are acquired at a high frame rate of 6000 shots/s for a period of 80 ms. The 480 ultrasonic lines that are acquired during that 80 ms period are highly correlated since the patient's organ (e.g. liver) does not significantly move during such a short period of time. As a result, the real contribution of the 480 ultrasonic lines or echo signals acquired during stiffness measurements to the CAP measurement is relatively poor. Even when the probe is not moved during an examination with a FIBROSCAN® (an ultrasound-based elastography apparatus for measuring the stiffness (or elasticity) and ultrasound attenuation of tissues and organs), the liver itself moves due to respiratory motions and therefore the measurements of stiffness are done in different locations. The operator typically performs 10 measurements. It was found that the spatial averaging obtained with these 10 measurements is appropriate for stiffness estimation but insufficient for CAP.

Furthermore, carrying out a CAP measurement during imaging, as opposed to solely during stiffness measurement as in conventional methods, is not intuitive because CAP is now measured with data or echo signals acquired from different locations in the liver other than those used for making stiffness measurements. Indeed, regardless of whether the probe moves during examination of the patient's liver, the patient's liver will necessarily move during examination due to respiratory motions. As a result, data or echo signals acquired during imaging and data or echo signals acquired during stiffness measurements will be captured from different locations in the liver. Equally important is the fact that, as will be appreciated by the skilled artisan, during imaging of the liver (i.e. when the operator moves the probe over the patient's liver to image it), many ultrasonic lines or echo signals are acquired from locations in the patient's abdomen other than liver. As a result, many ultrasonic lines or echo signals that cannot be used to determine CAP are generated during imaging of the liver. In the disclosed technology, as will be explained hereinafter, "bad" ultrasonic lines or echo signals that are collected during imaging are excluded using one or more quality criteria.

The new system and method for carrying out CAP measurements enable one to collect a large number of ultrasonic lines during a much longer period of time than in conventional methods, which significantly improves the spatial averaging of the acquired ultrasonic lines and significantly reduces the variability of the CAP value. Surprisingly, it was found that the variability of the CAP value determined according to the disclosed technology can be significantly reduced, e.g. by a factor 4. It will further be appreciated that the significant improvement in the determination of the CAP value is not done at the expense of stiffness measurements.

In an embodiment, there is provided a method for measuring an ultrasound parameter of a viscoelastic medium to be characterized with an elastography system configured to generate a shear wave in a region of interest, the elastography system including an ultrasound transducer configured to emit a sequence of ultrasound shots and to receive corresponding echo signals from the region of interest, and a processor programmed to alternately operate at least in a first mode and a second mode, wherein in the first mode, the processor is programmed to generate a sequence of ultrasound shots to measure an attenuation of ultrasound signals in a tissue; and wherein in the second mode, the processor is programmed to control the elastography system to induce a shear wave in the tissue; and to generate a sequence of ultrasound shots to track how the tissue in the region of interest is moved by the shear wave, the method comprising:

when the processor operates in the first mode, generating the sequence of ultrasound shots to the region of interest and receiving corresponding first mode echo signals from the region of interest;
recording first mode ultrasound attenuation values associated with the received first mode echo signals, and calculating a value of the ultrasound parameter using the first mode ultrasound attenuation values.

In some embodiments, the shear wave can be generated by an actuator or by an acoustic speaker.

In some embodiments, ultrasound is transmitted into the tissue of a subject at a relatively slow pulse repetition frequency such as between 10-100 pulses/second and in particular at a rate of (20+/−5) pulses/second. It is relevant to keep the rate slow enough in order not to exceed the acoustic output power upper limits specified by the FDA in the USA (2003). Ultrasound echo signals received from the pulses are analyzed in the frequency domain to estimate the attenuation of the signals versus frequency. Multiple attenuation measurements are collected over a period of time in order to produce a CAP measurement. In some embodiments, the received ultrasound echoes and attenuation measurements are compared to one or more quality metrics before being added to the accumulation of measurements used to produce a CAP measurement. In some embodiments, the ultrasound echo signals that are received and processed to generate the ultrasound attenuation values are those obtained when the elastography system operates in the first mode, i.e. the imaging mode, as opposed to when the elastography system operates in the second mode, which corresponds to the mode when a shear wave is generated and tracked to measure elasticity of the region of interest.

In some embodiments, the ultrasound system produces a display of "good" and "bad" first mode echo signals (i.e. the echo signals that are received during the imaging mode or first mode of operation of the elastography system) so that the user can visually determine if they are aiming an ultrasound probe in an area of homogenous tissue. In order to measure CAP, the "good" echo signals are selected using one or more quality criteria. CAP measurements are calculated by a processor and displayed to the user when a sufficient number of good attenuation values have been accumulated. The method according to the disclosed technology may comprise displaying the value of the ultrasound parameter that is calculated using the first mode ultrasound attenuation values.

In some embodiments, the first mode ultrasound echo signals are not used to compute a CAP measurement unless the signals are sufficiently decorrelated from previously received first mode echo signals. In other words, the system selects ultrasound lines that are different than those already captured. In some embodiments, attenuation values from the received echoes are not used to compute a CAP measurement unless the attenuation values lie within a predetermined range of values. In an embodiment, this predetermined range may be between 100-500 db/m. It will be appreciated that the "good" ultrasound lines can be selected first before selecting the ultrasound lines that are different. Alternatively, the ultrasound lines that are different can be selected first before selecting the "good" ultrasound lines.

In some embodiments, the system produces a histogram of attenuation values. A processor is programmed to fit a mixture of Gaussian or other bell-shaped distributions to the histogram to compute the most likely CAP measurement from the received echo signals. The likely error in the measurement can also be estimated from the Gaussian or bell-shaped distribution.

In some embodiments, attenuation values from the received echoes are not taken into account to calculate the value of the ultrasound parameter unless a coupling coefficient associated with the received echo considered is past a predetermined threshold value, the coupling coefficient being representative of a coupling force between the ultrasound transducer and a skin of a patient for whom the viscoelastic medium is to be characterized.

It will be appreciated that, according to the disclosed technology, the different embodiments presented above can be combined together, according to all technically possible combinations.

In an embodiment, there is provided a method for measuring an ultrasound parameter of a viscoelastic medium to be characterized with an ultrasound system including an ultrasound transducer configured to emit a sequence of ultrasound shots and to receive corresponding echo signals from a region of interest, and a processor programmed to generate, in a first mode, a sequence of ultrasound shots to measure an attenuation of ultrasound signals in a tissue, the method comprising:
  generating the sequence of ultrasound shots to the region of interest and receiving corresponding first mode echo signals from the region of interest, wherein the sequence of ultrasound shots are generated at a repetition rate of under 100 pulses/second for a period of time of at least 5 seconds;
  recording first mode ultrasound attenuation values associated with the received first mode echo signals, and
  calculating a value of the ultrasound parameter using the first mode ultrasound attenuation values.

In an embodiment, there is provided a system for measuring ultrasound attenuation in a region of interest in a tissue sample, comprising:
  an ultrasound transducer configured to emit a sequence of ultrasound shots and to receive corresponding echo signals from a region of interest; and
  a processor that is programmed to alternately operate in a first mode and a second mode, wherein in the first mode, the processor is programmed to
  generate a sequence of ultrasound shots to measure an attenuation of ultrasound signals in the tissue; and
    in the second mode, the processor is programmed to generate a sequence of ultrasound shots to track how the tissue in the region of interest is moved by a shear wave;
  wherein the ultrasound shots to measure the attenuation of ultrasound signals are transmitted outside of a time period when the processor is operating in the second mode.

In particular, the processor may be programmed so that, when it operates in the first mode, the shots of the sequence of ultrasound shots are transmitted at a shot repetition rate of under 500 shots/second, for example of under 100 shots/second, for example between 15 and 25 shots/second.

The processor may also be programmed to determine a quality of echo signals received from ultrasound shots obtained when the processor is operating in the first mode, and to determine the attenuation of ultrasound signals with echo signals having a desired quality level. In particular, the processor may be programmed to determine a quality of an echo signals based on one or more of a correlation between sequential echo signals and comparing an attenuation of the echo signal with a range of expected attenuation values.

The ultrasound parameter mentioned above is representative of, for example equal to, an attenuation of ultrasound signals in the viscoelastic medium, such as the controlled attenuation parameter (CAP).

The inventors have observe that a value of the ultrasound parameter, that is calculated using ultrasound attenuation values associated with several successive ultrasound shots, is much more reproducible when these ultrasound shots are generated for a long period of time, of at least 2 seconds, than when they are generated at high rate, for a period of time lasting only for a fraction of a second.

Without being bound by any theory, a possible explanation for this striking difference is the following. A single echo signal, backscattered by the medium, comprises a speckle-like component consisting of strong fluctuations (see the echo signal 50 of FIG. 1, for instance). For this and other reasons, a single value of the ultrasound attenuation determined from such an echo signal is thus subject to high variability. And if the ultrasound shots transmitted to probe the medium are generated with a high repetition rate, for a short period of time only, then, the position of the ultrasound transducer, or the one of the organ/tissue to be characterized does not change much from one ultrasound shot to the other. Hence, in such a situation, the speckle like component mentioned above remains substantially the same, from one echo signal to the other. Thus, the different attenuation values determined from the different echo signals received are not independent from each other. These different values may even substantially identical. So, taking into account such set of values, for instance by calculating an average of these values (or by means of another statistical analysis of this set of values), does not significantly improve the accuracy or repeatability of the measurement of ultrasound attenuation.

By contrast, if the ultrasound shots transmitted to probe the medium are generated for a period of time that lasts a few seconds or more, then, the organ/tissue moves relative to the ultrasound transducer, during this period of time, as a result of respiration and/or transducer displacements. Due to this relative displacement, the speckle like component mentioned above changes during the period of time used to probe the medium. The different echo signals received by the system are then at least partially decorrelated, and the different values of ultrasound attenuation determined from these different echo signals correspond to somehow independent measurements. Averaging these values thus lead to a final ultrasound attenuation value having an improved accuracy and/or repeatability. In addition, the displacement mentioned above enables, by spatial averaging over a wide area of the organ/tissue to characterize, to smoothen potential inhomogeneities of the structure of this organ/tissue.

According to an optional feature of the method described above, the sequence of ultrasound shots is transmitted at a shot repetition rate of under 500 shots/second, for example of under 100 shots/second, and in an embodiment between 15 and 25 shots/second. In particular, the repetition rate can be between 15 and 25 shots/second while the ultrasound shots are generated for a period of time of 20 seconds at least.

With such repetition rates, there is enough time between two successive shots for the organ/tissue to move relative to the ultrasound transducer. As a result, each shot contributes in a meaningful manner to the improvement of the accuracy/repeatability of the final value of ultrasound attenuation mentioned above. By contrast, if the sequence of ultrasound shots were transmitted at a high repetition rate, of a few kilohertz for instance, many of the transmitted shots would not contribute to the accuracy/repeatability improvement mentioned above, thus uselessly increasing the computing resources required to process the received echo signals and uselessly increasing the ultrasound emissions (whose excess may be harmful to the subject whose organ/tissue is being characterized, or to the professional carrying on this characterization). Still, even if it would not be optimal, the method described above could be implemented using high repetition rates (higher than 500 shots/second), as long as the sequence of ultrasound shots lasts for 2 seconds at least.

It will be appreciated that, according to the disclosed technology, the different embodiments presented herein can be combined together, according to all technically possible combinations.

BRIEF DESCRIPTION OF THE DRAWINGS

Other characteristics and benefits of the disclosed technology will become clear from the description which is given below, by way of example and non-restrictively, with reference to the figures, in which:

FIG. 2 is a block diagram of a method for computing CAP measurements in accordance with some embodiments of the disclosed technology;

FIG. 3B illustrates a representative display showing a CAP measurement, a histogram of attenuation measurements, TM-mode ultrasound image data from a region of interest and an indicator of whether the ultrasound attenuation data meet one or more quality criteria in accordance with some embodiments of the disclosed technology;

FIG. 3C illustrates a representative display showing a CAP measurement, a dual peak histogram of attenuation measurements, TM-mode ultrasound image data from a region of interest and an indicator of whether the ultrasound attenuation data meet one or more quality criteria in accordance with some embodiments of the disclosed technology;

FIG. 4 illustrates a timing diagram for a system that determines CAP measurements and VCTE tissue stiffness measurements in accordance with some embodiments of the disclosed technology;

FIG. 6 is representative of a user interface showing both CAP and stiffness measurements in accordance with an embodiment of the disclosed technology;

DETAILED DESCRIPTION

Figure 1:
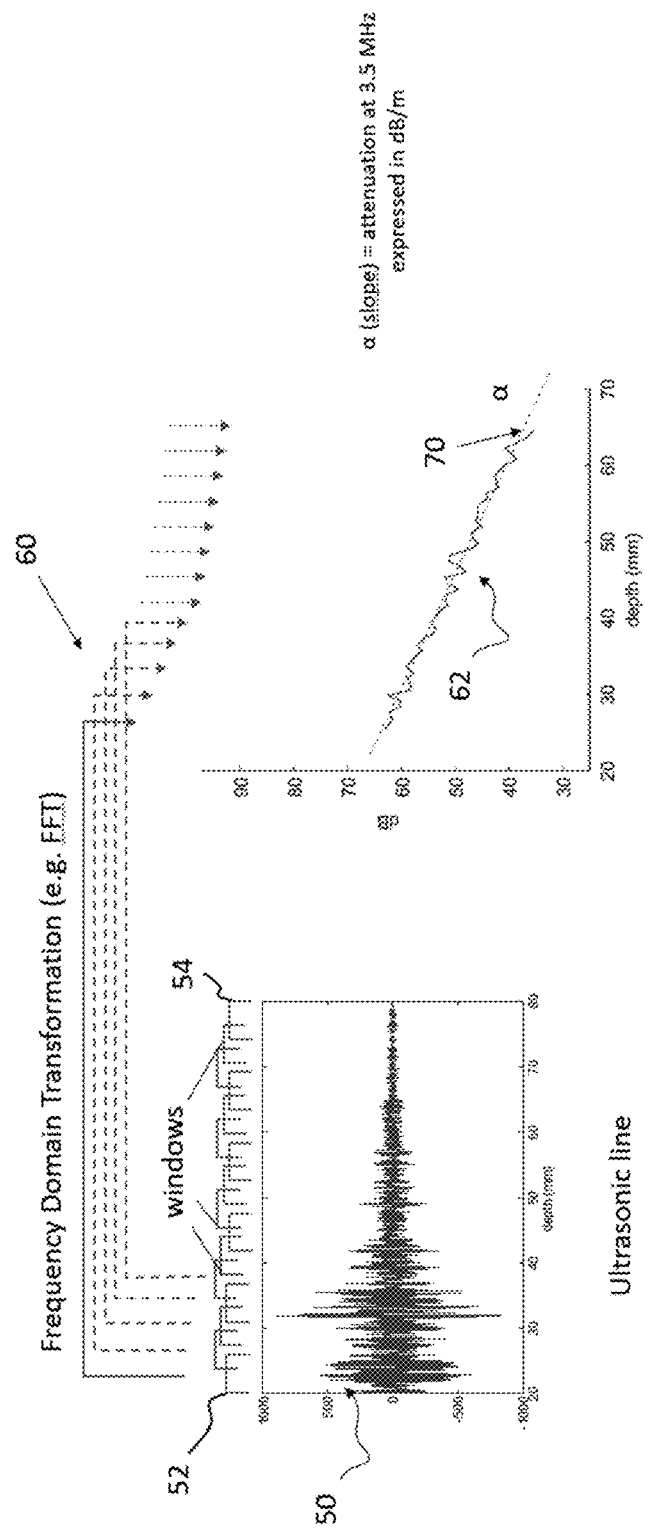
FIG. 1 illustrates how estimates of ultrasound attenuation are made in the frequency domain in accordance with some embodiments of the disclosed technology.

As will be discussed in further detail below, the disclosed technology relates to systems and methods for estimating tissue characteristics from the measured attenuation of ultrasound signals that are transmitted in a body. In some embodiments, the tissue characteristic is a CAP value that is indicative of the amount of fat present in the liver. In the currently available FIBROSCAN® system (an ultrasound-based elastography apparatus for measuring the stiffness (or elasticity) and ultrasound attenuation of tissues and organs) from Echosens, the system measures the stiffness and ultrasonic attenuation caused by tissue characteristics in a human or animal liver rapidly and in a non-invasive and reproducible manner.

In vibration controlled transient elastography (VCTE), a transient shear wave is generated by a vibrator such as an electromechanical vibrator or acoustic speaker, that is placed adjacent the medium to be characterized such as on the skin in the area of the subject's liver. The propagation of the shear wave is then monitored using a series of ultrasonic acquisitions (shots) produced by an ultrasound transducer with a high rate of repetition. Each ultrasound acquisition corresponds to at least one ultrasound emission and reception. Each ultrasound emission can be associated with the detection and on-the-fly recording of the echoes generated by the reflective particles present in the analyzed medium for a defined range of depths. The reflected ultrasound signals are processed by correlation or other signal pattern matching technique to determine the movements of the tissue that are caused by the propagation of the shear wave as a function of time and position in the medium. An analysis of the movements enables the speed of the shear wave inside the viscoelastic medium to be determined, and therefore the elasticity or stiffness of the tissue, to be determined.

In the currently available FIBROSCAN® system, the ultrasound pulses for VCTE that are used to determine the speed of a shear wave in the body are analyzed to determine the CAP measurements. Validation of the CAP measurements is based on the measurements of the tissue stiffness. If the tissue stiffness measurements are invalid, then the corresponding ultrasound attenuation measurements are discarded. This is therefore an after-the-fact validation. In other words, the FIBROSCAN® system validates the CAP measurements using the results from the transient elastography readings, i.e. using echo signals that are received during the second mode of operation of the FIBROSCAN® system. These measuring techniques are described in patent applications FR 2949965 (published as U.S. 2012190983) and FR 2978657 (published as U.S. 2014249415), which are herein incorporated by reference.

Another issue with using the same ultrasound signals that detect the shear wave speed (VCTE acquisition) to determine CAP measurements is their high rate of repetition or pulse repetition frequency (PRF) and associated short duration of acquisition. In some systems, the PRF of the shear wave tracking ultrasound pulses is 6000 pulses/sec and the acquisition lasts only 80 ms which results in 480 ultrasonic lines or echo signals for one stiffness measurement. Because the duration of the acquisition is rather short compared to how the organs move due to breathing, heart beats or the like, the return ultrasound signals are often highly correlated and thus contain redundant data, which is not representative of a larger area of tissue in term of ultrasonic attenuation. Given that a typical examination procedure consists of less than 10 valid measurements of stiffness, one can estimate that the total number of ultrasonic lines or echo signals acquired is high: 4800 as each measurement corresponds to a deck of 480 lines. However, each measurement only lasts 80 ms during which the ultrasonic lines barely decorrelate. Therefore, the true contribution of the 480 lines of a single deck is rather low. Hence the duration of data acquisition for ultrasonic attenuation is only 800 ms, less than one second in the current FIBROSCAN® device setting. Even though the number of ultrasonic lines acquired for CAP measurement is high (~4800) in the current FIBROSCAN® device setting, one notices that not only the total acquisition time is short (<1 second) but the actual number of ultrasonic lines or echo signals that contribute to the CAP measurement is rather small: ~10 due to the poor decorrelation in between ultrasonic lines acquired for one shear wave speed measurement. The inventors have determined that a good determination of ultrasonic attenuation requires a high spatial averaging that may not be obtained with this method. This high correlation rate and associated poor spatial averaging may contribute to the variability in measuring an ultrasound parameter such as the CAP.

Another potential cause of the variability of the measured values is the presence of varied areas (heterogeneities) that modify the local measurements. In the case of a human or animal liver, such variability can be caused by the presence of a vein or vessel traversing the region in which the measurement is made.

To address these and other issues, the disclosed system processes ultrasound signals or echo signals acquired during a much longer duration at a lower rate. In one embodiment, the ultrasound is transmitted into the body to generate an image such as a TM-mode image and/or a A-mode image of the tissue under examination. This image is used by the operator to locate the region of interest over several seconds, typically 10 seconds which is definitely much larger than the 80 ms of a VCTE acquisition that is used to detect the shear wave speed. The ultrasound signals are transmitted into a body and reflected from scatterers at a PRF that is selected such that the body can move over the period of several acquisitions. In one embodiment, the PRF is less than 100 shots/sec and for example less than 50 shots/sec, such as (20+/−5) shots/sec. The lower rate of the ultrasound shots compared to the PRF used for elastography allows the return echo data to be more uncorrelated and therefore representative of a larger sampling area as the probe and the tissues are moving. By using a lower PRF associated with a longer acquisition duration, the disclosed system accumulates attenuation values over a long period of time, which improves significantly the spatial averaging, without adding too much redundant ultrasound data and without increasing the average acoustic output power delivered to the patient.

The inventors have determined that measuring ultrasound attenuation in the time domain in not very accurate when calculating CAP measurements. To overcome this limitation, the system of the disclosed technology estimates the attenuation from an analysis of the received echo signals in the frequency domain. FIG. 1 illustrates one technique for determining ultrasound attenuation in accordance with the disclosed technology. An ultrasound signal 50 represents a line of received echo data. The return echo data is digitized and analyzed for a time period beginning at a time 52 that corresponds to the beginning of a desired region of interest (e.g. depth range) and extends to a time 54 that marks the end of the region of interest. In the embodiment of FIG. 1, the depth range extends from 20 mm to 80 mm, which corresponds to the depth range under the skin where liver is located. The time period is sub-divided into a number of smaller time segments or windows (of several μs, typically 5 μs), each corresponding to a portion of the depth range in the region of interest. In some embodiments, the windows can partly overlap, as shown in FIG. 1. The digitized ultrasound signal for each sub period or window is converted into the frequency domain 60 using a fast Fourier transform (FFT) or other time domain to frequency domain transformation. The result is a plot of the magnitude of the frequency components present in the received echo for each time period versus depth.

The amplitude of the frequency components present in the received echo for each time period versus depth is plotted or stored in a non-transitory computer readable memory. In the example shown, a line 62 represents the attenuation of the echo signals at 3.5 MHz, which corresponds to the frequency bandwidth used during measurement of the ultrasound attenuation. The slope of absorption at 3.5 MHz is determined and a best fit line 70 such as a linear interpolation is used to estimate the slope/attenuation at the frequency of the ultrasound echo signals received. In the example shown, the frequency used is 3.5 MHz. However, other bandwidth frequencies could be used depending on the transducer selected for the subject (e.g. pediatric, normal, obese subjects etc.). In accordance with embodiments of the invention, the measurement of the slope is a measurement of the CAP value. In other embodiments of the disclosed technology, measurements at more than one frequency (e.g. a frequency different than 3.5 MHz) could be done so that multiple slope/attenuations could be determined in order to determine the CAP value.

FIG. 2 illustrates the basic steps of a method 100 for measuring an ultrasound parameter according to some embodiments of the disclosed technology. Beginning at 102, the system generates a sequence of ultrasound shots. The ultrasound shots are emitted by an ultrasound transducer placed in proximity to the medium to be characterized. The ultrasound signals propagate within the medium to be characterized are at least partially reflected by the analyzed medium. Reflected ultrasound echoes are digitized and stored in a computer readable memory. According to one implementation, the emission and recording of the ultrasound signals is performed using the same ultrasound transducer. However, it would be possible to use a transducer having separate transmit and receive elements.

According to one implementation, the ultrasound shots are emitted with rate of repetition of less than 50 Hz and for example equal to 20+/−5 Hz. The choice of a 20 Hz frequency is favorable for real time display of a TM-mode or A-mode image as a human eye typically captures 25 images per second. As indicated above, this low rate of repetition allows recording of the reflected ultrasound signals that are decorrelated with one another due to the difference in time of acquisition compared to the respiratory motion speed. With a repetition frequency of 20 Hz, ultrasound signals are acquired every 50 ms. The respiratory frequency is typically between 12-50 cycles per minute which translates to 1.2-5.0 seconds. The displacement of an organ such as liver is typically of several centimeters. Liver motion speed due to respiration is typically of the order 1 centimeter per second. In 50 ms, the displacement would be of 2 mm which is enough to decorrelate the ultrasound signal. Using decorrelated ultrasound signals improves the reliability of the measurements while reducing measuring errors.

At a step 102, the method accumulates (ACC) valid ultrasonic attenuation values. In some embodiments, each ultrasound line or echo signal is associated with a quality criteria. This quality criteria is used to automatically reject ultrasonic lines that do not meet some predetermined characteristics. Only attenuation values associated with an acceptable quality criteria are used to compute the final CAP measurement. In some embodiments, the quality criteria can be computed based on several coefficients which are compared to one or more thresholds. In some embodiments, a coefficient can be used to select ultrasonic lines or echo signals that are sufficiently decorrelated. This coefficient can be a correlation coefficient computed from the correlation between successive ultrasonic lines previously acquired at different times.

In particular, the correlation coefficient associated to the ultrasonic line considered, which is used to assess this ultrasonic line quality, can be a correlation coefficient between all or a part of this ultrasonic line, and another ultrasonic line received before it (such as the ultrasonic line received just before the ultrasonic line whose quality is to be assessed).

The correlation coefficient between the ultrasonic line considered and another, previously received ultrasonic line can be calculated by taking into account several "local" correlation coefficients associated respectively to different parts of the ultrasonic line considered (for instance by averaging these different local correlation coefficients). In such a case, each of these local correlation coefficients is representative of a correlation between the part of the ultrasonic line considered that is associated to this local correlation coefficient, and the other ultrasonic line received previously.

The correlation coefficient is a number representative of a degree of correlation, that is to say a degree of similarity between the two series of numerical values or data considered (namely, between the ultrasonic line whose quality is to be assessed and a previous ultrasonic line or between parts of these ultrasonic lines). The correlation coefficient can be obtained by means of different kinds of algorithms, for instance by means of a cross-correlation "slider dot product" calculation ("slider inner product"), or by means of a least-square algorithm enabling to evaluate a mismatch between the two series of numerical values or data considered.

If the correlation coefficient is above a predetermined threshold value, then the data is deemed too correlated and the attenuation value of the ultrasonic line is not used to compute to compute the final CAP measurement. In this case, the correlation coefficient past a predetermined threshold value should be a correlation coefficient below the threshold value for the line to be considered.

In practice, setting the predetermined threshold to 80% (80 percent) of a reference value that corresponds to perfectly correlated signals enables to select attenuation values that are sufficiently independent from each other, and thus well suited for a subsequent statistical filtering (such as an averaging). In other words, an echo signal may be considered as sufficiently decorrelated, and may thus be taken into account to compute the final CAP measurement, when the correlation coefficient associated to this signal is below 80% of the reference value mentioned above. For example, when the correlation coefficient is a correlation coefficient between a part of the ultrasonic line considered and another ultrasonic line received previously, then, the part of the ultrasonic line considered and the ultrasonic line received previously may be considered as perfectly correlated when the part of the ultrasonic line is found, identical, or multiplied by a proportionality coefficient, within the ultrasonic line received previously (at a position, within the ultrasonic line received previously, that may be different from the position of the part within the ultrasonic line whose quality is to be assessed). When the correlation coefficient is calculated by means of a "slider dot product" normalized correlation calculation, for instance, then the reference value is equal to 1, while the predetermined threshold is equal to 0.8.

In some embodiments, a coefficient can be used to select ultrasonic lines that present good characteristics such as the absence of vessel wall interface on the ultrasonic line. This coefficient can be named a quality coefficient. This coefficient can be for example the coefficient of determination ($R^2$) of a linear regression applied to the ultrasonic line. In some embodiments, a coefficient can be used to select ultrasonic lines with an attenuation value that is between an expected range, for example in the 100-400 dB/m range. In such case, attenuation values outside of the expected range are ignored as they are considered as outliers. In a particular embodiment of the invention, at least two quality criteria are used: a first quality criteria is first used to select the ultrasonic lines or echo signals that are sufficiently decorrelated and a second quality criteria is then used to select ultrasonic lines or echo signals with an attenuation value that lies with an expected range, or vice versa. However, this is not limiting, other quality criteria that are predetermined to automatically reject ultrasonic lines or echo signals that do not meet some predetermined characteristics could be used in other embodiments of the invention. For example, in an embodiment, the quality criterion includes a correlation criterion and the processing of the received first mode echo signals includes associating each one of the received first mode echo signals with a correlation coefficient and selecting each of the received first mode echo signal having the correlation coefficient past a predetermined threshold value to determine, among the received first mode echo signals, echo signals that are sufficiently decorrelated. The correlation coefficient may be calculated based on the received first mode echo signals and previously received first mode echo signals which may include from one to N previously received first mode echo signals.

Alternatively, instead of analyzing the received first mode echo signals with previously received first mode echo signals to determine a correlation coefficient and a correlation criterion, each echo signal may be analyzed separately and individually to determine whether the echo signal satisfies several predetermined characteristics (e.g. signal intensity, profile of the echo signal . . . ), which correspond to a quality criterion. Furthermore, the one or more quality criteria may include an attenuation criterion that is defined by a predetermined range of ultrasound attenuation values and the processing includes selecting each of the first mode ultrasound attenuation values that are within the predetermined range. In an embodiment, two or more of the quality criteria can be used to select the received first mode echo signals to determine the CAP value.

According to one implementation, a processor is programmed to analyze a number of valid attenuation values at a step 106 (CALC) to compute a CAP measurement. The number of valid attenuation values is the number of attenuation values for which the quality criteria is acceptable. In some embodiments, the system accumulates at least a predefined number of valid attenuation values before a CAP measurement is computed. The valid attenuations are selected with the above one or more quality criteria. The predefined numbers of valid attenuation values can be selected between 100 and 10000. It can also be associated with an equivalent duration of acquisition range such as 5 to 500 seconds which corresponds to a range of 100 to 10000 attenuation values for a rate of 20 Hz. The same duration of acquisition range would correspond to a range of 1000 to 100000 attenuation values for a rate of 200 Hz. In some embodiments, once a sufficient number of valid attenuation measurements are obtained, the processor constructs and analyzes a histogram of the valid accumulated ultrasonic attenuation values. In this case, each bar of the histogram represents the number of ultrasound echo signals received with a given ultrasonic attenuation value. As will be explained in detail below, the histogram is analyzed to determine the peak value (e.g. the value of the most common attenuation) and other statistics about the histogram such as standard deviation. Such an analysis can be performed by calculating a Gaussian distribution to fit the histogram. This fit can be performed with a single peak or a multiple peaks approach (Gaussian mixture).

According to one implementation, the CAP measurement is the median or the mean of the valid attenuation values.

According to one implementation, the CAP measurement is the weighted mean of the attenuation values. Each attenuation value is associated with a coefficient used to weight the attenuation values depending on their significance.

According to one implementation, the CAP measurement is associated with a dispersion indicator which can be the interquartile range (IQR=Q3−Q) or the standard deviation of the set of valid attenuation values.

Once the attenuation data are analyzed, the method displays a CAP measurement (DSP) at 108 that is computed from the number of valid accumulated ultrasonic attenuation values. The use of a multiple peaks approach can be used to display to the user several CAP measurements when the to-be-measured organ is heterogeneous.

Beneficially, the display at 108 is determined in real time (i.e. during the imaging mode of the medium) by the processor from the number of valid accumulated ultrasonic attenuation values, which enables the operator to check the state of progress of the examination. When used in conjunction with shear wave speed measurements, the display may only be updated when stiffness measurements are being performed in order not to alter the way the current FIBRO-SCAN® devices work.

According to one implementation, a gauge type indicator shown to the operator graphically displays a representative number (number of valid ultrasonic attenuation values, percentage compared to a target, numeric indicator, acquisition duration in seconds, etc.) of valid ultrasonic attenuation values used to compute the CAP measurement selected to ensure a quality measurement. The greater the number of attenuation values used, the more reliable the CAP value will be. The gauge type indicator can indicate whether the number of valid ultrasound attenuation values is less than or greater than the desired number.

Figure 3A:
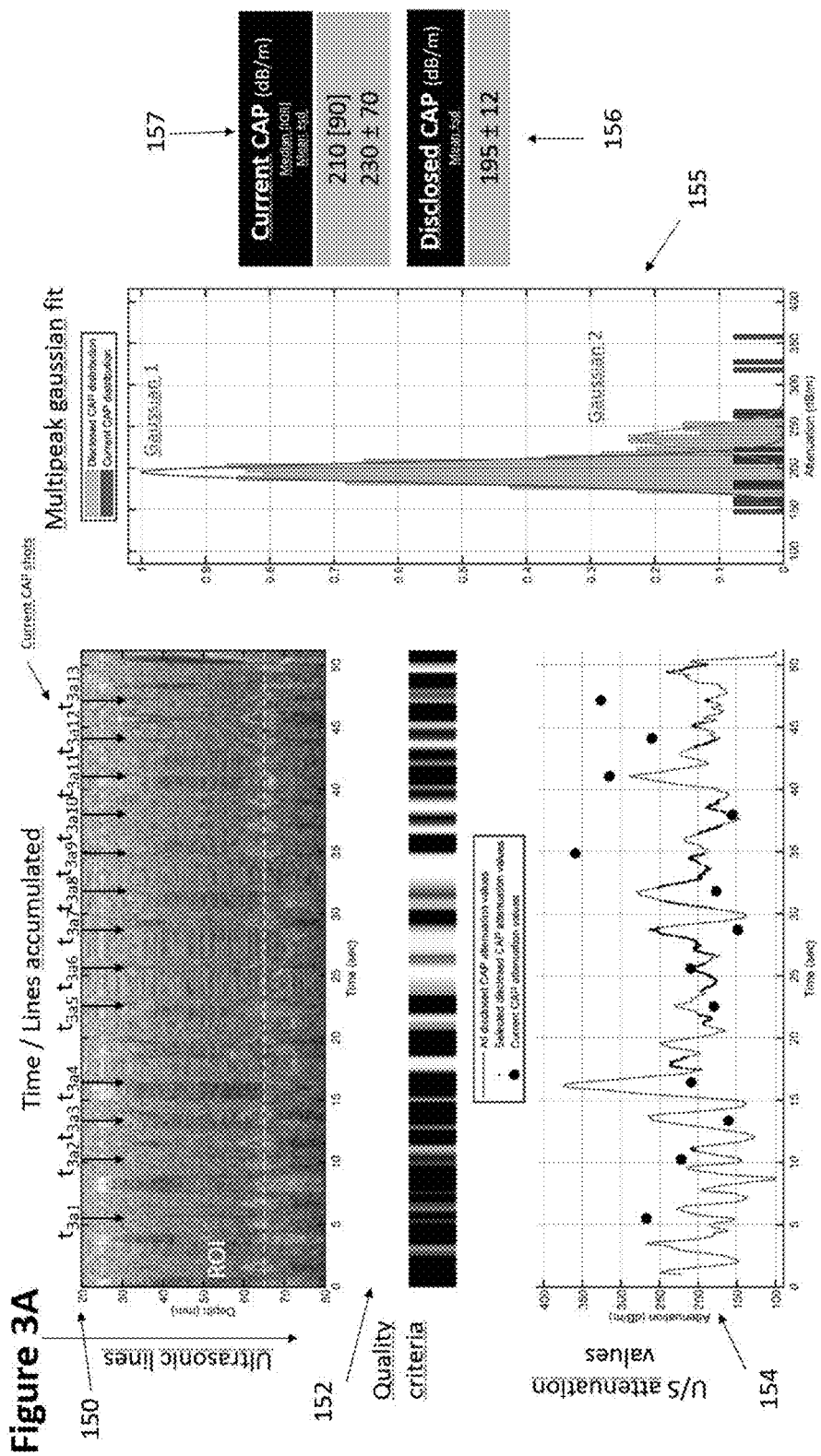
FIG. 3A illustrates a representative display showing a CAP measurement, a histogram of ultrasound attenuation values, TM-mode ultrasound image data from a region of interest and an indicator of whether the ultrasound attenuation data meet one or more quality criteria in accordance with some embodiments of the disclosed technology.

FIGS. 3A-C illustrate how one embodiment of the system collects ultrasound signals and computes a CAP measurement. FIGS. 3A-C show data obtained on a human patients. As shown in FIG. 3A, an ultrasound image is produced from the received ultrasound echo data. In some embodiments, the echo data is A-line data (e.g. received along a single linear path in the direction of interest). Multiple A signals are displayed side by side to produce a TM-mode image 150 showing how the tissue on the single line moves over time (horizontal axis). The TM-mode image 150 represents the ultrasonic lines or echo signals received over time during the first and second modes of operation of the elastography system. Ultrasonic lines are plotted as a function of time in seconds. In TM-mode image 150, the imaging of the medium lasts over 50 seconds. Also represented in the TM-mode image 150 is the region of interest (ROI) which is bound by two dashed lines at 25 mm and 65 mm, which corresponds to the depth under the patient skin where liver is typically located. The TM-mode image 150 also schematically shows the instants $t_{3a1}$, $t_{3a2}$, $t_{3a3}$, $t_{3a4}$, $t_{3a5}$, $t_{3a6}$, $t_{3a7}$, $t_{3a8}$, $t_{3a9}$, $t_{3a10}$, $t_{3a11}$, $t_{3a12}$ and $t_{3a13}$ when the operator actuates the elastography device to generate a shear wave. At each of these instants and for a duration of 80 ms, the elastography system operates in the second mode (i.e. the stiffness measurement mode). Thus, FIG. 3A shows received ultrasound echoes when the elastography system operates in the first and second modes (i.e. the imaging mode and the stiffness measurement mode). However, the received ultrasound echoes (represented in TM-mode image 150) associated with the second mode are barely visible in image 150 because, as explained above, the second mode lasts 80 ms (i.e. the duration of the second mode beginning at instants $t_{3a1}$, $t_{3a2}$, $t_{3a3}$, $t_{3a4}$, $t_{3a5}$, $t_{3a6}$, $t_{3a7}$, $t_{3a8}$, $t_{3a9}$, $t_{3a10}$, $t_{3a11}$, $t_{3a12}$ and $t_{3a13}$ is 80 ms), which is small compared to the total duration of 50 seconds. In other words, each of the 80 ms time periods starting at instants $t_{3a1}$, $t_{3a2}$, $t_{3a3}$, $t_{3a4}$, $t_{3a5}$, $t_{3a6}$, $t_{3a7}$, $t_{3a8}$, $t_{3a9}$, $t_{3a10}$, $t_{3a11}$, $t_{3a12}$ and $t_{3a13}$ and corresponding to the second mode include 480 ultrasonic lines, which are barely visible in the image 150 (due to the image resolution). By contrast, ultrasonic lines acquired during the first imaging mode are more visible since they are acquired every 50 ms.

Below the TM-mode image 150 are two plots 152, 154. The plot 154 represents the attenuation values computed for the corresponding A-lines directly above in the TM-mode image 150, which are stored in a computer readable memory. In some embodiments, the attenuation data is flagged or otherwise marked in the memory if the data are "good," which in some embodiments means the attenuation data are within a predefined guard band and the echo data used to compute the attenuation values meet the correlation requirements. Attenuation values outside of the guard band or echo data not meeting the correlation requirements are marked as "bad" data. The plot 152 represents a record of the good and bad values of the attenuation data. The good data correspond to the ultrasonic lines that satisfy the predefined one or more quality criteria discussed hereinabove. For example, in FIG. 3A, two quality criterion have been used: a first quality criteria to determine the ultrasonic lines that are sufficiently decorrelated and a second quality criteria to determine the ultrasonic lines that have attenuation values that lie within a predetermined range, of for example 100-400 dB/m, or an extended range of for example 50-500 dB/m. In the embodiment shown, the plot 152 includes a number of dark colored sections marking bad data where the quality criteria is not acceptable (i.e. the ultrasonic lines are rejected by either the first quality criteria or the second quality criteria or by both the first and the second quality criteria). The plot 152 also includes a number of white sections, marking areas of "good" ultrasound signal data where the quality criteria is acceptable (i.e. the ultrasonic lines satisfy both the first and second quality criteria). If all the ultrasound signal data were "good", the entire display 152 would be colored with no dark sections. As will be appreciated, other markers besides color could be used to mark the good and bad attenuation data such as shading, cross-hatching etc. As will be appreciated the display 152 may not be displayed to the operator. If the plot 152 is only to be read by the processor, the plot can be coded such as by storing a logic "1" for each good attenuation/echo signal line (good quality criteria) or storing a logic "0" for each bad attenuation/echo signal line (bad quality criteria). By analyzing the plot 152, the processor is able to determine if the probe is oriented at a good spot in the liver to measure CAP values and can prompt the user to change the orientation of the probe if needed.

Plot 154 of FIG. 3A also shows CAP attenuation values obtained (a) conventionally, i.e. during shear wave tracking or elasticity measurements (identified as "Current CAP attenuation values" and shown with large black circles in FIG. 3A and (b) according to an embodiment, i.e. outside of the time period of shear wave tracking or elasticity measurements (identified as "Selected disclosed CAP attenuation values" and shown with a small black circle in FIG. 3A). As can be seen in plot 154, each large black circle corresponds to instants $t_{3a1}$, $t_{3a2}$, $t_{3a3}$, $t_{3a4}$, $t_{3a5}$, $t_{3a6}$, $t_{3a7}$, $t_{3a8}$, $t_{3a9}$, $t_{3a10}$, $t_{3a11}$, $t_{3a12}$ and $t_{3a13}$. Conventional CAP attenuation values significantly vary over time in plot 154.

In an embodiment, a complementary criteria can be used to select the ultrasonic lines relates to the coupling between the ultrasound transducer and the surface of the skin. Such a coupling can be represented by the applied force level applied to the skin by the probe. As a matter of fact a good coupling is desired between the ultrasound transducer and the surface of the skin. Only ultrasonic lines acquired with a minimum applied force could be included for computation. A minimum applied force of 1 Newton can be used. For example, the one or more quality criteria include a coupling criterion representative of a coupling force between the ultrasound transducer and a skin of a patient for whom the viscoelastic medium is to be characterized, the coupling criterion defined by a predetermined range of coupling coefficient values (e.g. force values). The received first mode echo signals are processed by associating each of the received first mode echo signals to a coupling coefficient and selecting each first mode echo signal having the coupling coefficient past a predetermined threshold value.

A processor in the ultrasound system is programmed to analyze the good attenuation data that is captured by the system. For example, the processor may execute computer readable instructions, which are stored in a non-transitory memory of the disclosed system, for processing the ultrasonic lines and determining whether the ultrasonic lines pass the quality criteria, e.g. the first and the second quality criteria in FIG. 3A. Once the number of "good" attenuation data values accumulated exceeds some required minimum, the processor computes a histogram 155 of the values. In one embodiment, the suggested minimum number of good values is set to 400 or 20 seconds worth of good echo signals received at 20 shots/second. Such data need not be acquired sequentially. That is, some good ultrasound data may be interspersed with bad ultrasound data. More data than the desired minimum could be used to increase the accuracy of the computed histogram. As will be appreciated, other values for a desired minimum number of good attenuation values could be used. In some embodiments, the minimum number may be set by the system or could be set by the user. Different types of probes may have different minimums. For example, pediatric probes for use with children may have a requirement for a smaller minimum number of good data than those used with obese patients etc.

Once the operator decides to terminate the exam, the values are fixed and the system delivers the final CAP value (or CAP values if multiple peaks) which is representative of the fat content. This termination of the exam can be automatic when the number of valid ultrasonic values past a predefined threshold.

Once the histogram of the computed attenuation values is computed by the processor, the processor analyzes the histogram 155. In some embodiments, the processor fits a Gaussian curve to the histogram (single peak or multiple peaks). From the fitted Gaussian, statistical measurements such as the mean and standard deviations can be determined by the processor. Other statistical curve fittings could also be done. In some embodiments, knowing the Gaussian for the histogram allows the histogram to be mathematically shifted etc.

In the example shown in FIG. 3A, it can be seen that the histogram includes a major peak and a minor second peak. This type of histogram is typically indicative of a relatively homogeneous attenuation in the tissue where the concentration of fat deposits (steatosis) in the liver are relatively constant throughout the region of interest.

From the histogram of the attenuation data (plotted in light gray in FIG. 3A), a CAP 156 (shown as Disclosed CAP in FIG. 3A) measurement is calculated and displayed. In one implementation, the display of the disclosed system provides a mean value (here 195 dB/m) of the measured CAP as well as the standard deviation of the CAP value (here +/−12 dB/m). For comparison, FIG. 3A also shows the CAP value 157 ("current CAP") measured on the same patient during stiffness measurement (i.e. at instants $t_{3a1}$, $t_{3a2}$, $t_{3a3}$, $t_{3a4}$, $t_{3a5}$, $t_{3a6}$, $t_{3a7}$, $t_{3a8}$, $t_{3a9}$, $t_{3a10}$, $t_{3a11}$, $t_{3a12}$ and $t_{3a13}$), which corresponds to the CAP value measured according to the conventional method. As can be seen in FIG. 3A, the CAP value measured using the conventional method (its histogram being plotted in dark gray) ("Current CAP") provides a mean value that is similar to the one measured according to the disclosed technology. However, as will be appreciated by the skilled artisan, the standard deviation measured using the disclosed technology has been significantly reduced, in particular by a factor 6 in the present example. As a result, the disclosed technology significantly improves the accuracy of the measured CAP value, which makes that parameter a very good candidate to monitor liver steatosis in a clinical setting.

FIG. 3B shows a second ultrasound image 160 and plots 162 and 164 of the corresponding attenuation values associated with a second patient according to an embodiment. FIG. 3B shows similar plots as those shown in FIG. 3A. Also shown in FIG. 3B are the instants $t_{3b1}$, $t_{3b2}$, $t_{3b3}$, $t_{3b4}$, $t_{3b5}$, $t_{3b6}$, $t_{3b7}$, $t_{3b8}$, $t_{3b9}$ and $t_{3b10}$ when the operator actuates the elastography device to generate a shear wave. The gaussian fit 165 shows a single peak. This type of histogram is typically indicative of a relatively homogeneous attenuation in the tissue where the concentration of fat deposits (steatosis) in the liver are relatively constant throughout the region of interest. From the histogram of the attenuation data, a CAP 166 (shown as Disclosed CAP in FIG. 3B) measurement is calculated and displayed. In one implementation, the display of the disclosed system provides a mean value (here 220 dB/m) of the measured CAP as well as the standard deviation of the CAP value (here +/−23 dB/m). For comparison, FIG. 3B also shows the CAP value 167 ("current CAP") measured on the same patient during stiffness measurement (i.e. at instants $t_{3b1}$, $t_{3b2}$, $t_{3b3}$, $t_{3b4}$, $t_{3b5}$, $t_{3b6}$, $t_{3b7}$, $t_{3b8}$, $t_{3b9}$ and $t_{3b10}$), which corresponds to the CAP value measured according to the conventional method.

FIG. 3C shows a third ultrasound image 170 and plots 172 and 174 of the corresponding attenuation values associated with a third patient according to an embodiment. FIG. 3C shows similar plots as those shown in FIG. 3A. Also shown in FIG. 3B are the 20 instants $t_{3c1}$–$t_{3c20}$ when the operator actuates the elastography device to generate a shear wave. Comparing the plot of attenuation values 174 shown in FIG. 3C with the plot of attenuation values 154 shown in FIG. 3A, many more attenuation values are are classified as "good". A plot 172 also contains fewer dark lines marking bad ultrasound data compared with the plot 152 of FIG. 3A. The good attenuation values are accumulated and analyzed by the processor to compute a histogram 175. In the example shown, the Gaussian functions fitted to the histogram 175 includes two distinct peaks. In such an example, the dual peaks can inform a user that there are two zones of differing fat content (steatosis) in the region of interest or that the steatosis is not uniform in the liver. From the histogram of the attenuation data, a CAP 176 (shown as Disclosed CAP in FIG. 3C) measurement is calculated and displayed. In one implementation, the display of the disclosed system provides a mean value (here 292 dB/m) of the measured CAP as well as the standard deviation of the CAP value (here +/−26 dB/m). For comparison, FIG. 3C also shows the CAP value 177 ("current CAP") measured on the same patient during stiffness measurement (i.e. at instants $t_{3c1}$–$t_{3c20}$), which corresponds to the CAP value measured according to the conventional method.

Like in FIGS. 3A-C, it can be seen that the standard deviation measured using the disclosed technology has been significantly reduced, in particular by a factor 2 in the present example of FIG. 3C. Equally important is the fact that the disclosed technology for calculating the CAP value can now inform the operator of the presence of different zones of fat contents in the patient liver, as shown in FIG. 3C. Such information was difficult to obtain with the conventional method.

Once the histogram is analyzed, the processor computes a CAP value from the Gaussian curve. In some embodiments, the CAP measurement is determined according to the fit by a Gaussian function where:

$$f(Att) = A \times e^{-\frac{(Att-\mu_{CAP})^2}{2\sigma_{CAP}^2}}$$

$\sigma_{CAP}$ is the standard deviation of the Gaussian, i.e. of the CAP $\mu_{CAP}$ is the mean of the Gaussian, i.e. of the CAP Att is the ultrasound attenuation f(Att) is the Gaussian curve A is a constant However, other equations for computing the CAP measurement could also be used. In addition, as will be appreciated by those skilled in the art, other peak fitting methods may also be used.

FIG. 4 shows a timing diagram in which a system that performs both VCTE and CAP measurements can operate. As indicated above, the ultrasound system operates in an imaging mode (first mode), such as TM-mode, whereby a user can view the tissue in the region of interest during a time period 200. The system transmits short ultrasound bursts (e.g. 1-2 cycles of ultrasound at a center frequency such at 3.5 MHz (or another center frequency depending on the probe) at a relatively low PRF such as 20 shots/sec. Attenuation data are collected from each return echo signal. A PRF close to 20 Hz is favorable in order to update the display in real time. A higher PRF can be used but one must keep in mind that lowering the average acoustic output power presents important benefits in terms of safety and regulatory.

Once the user sees that the tissue is homogeneous or does not notice any anomalies in the return echo data, the user can press a button on the probe to generate a shear wave pulse in the subject's tissue. The speed of the shear wave is then tracked by the system by firing ultrasound pulses at a much higher PRF such as at 6000 shots/sec during a time period 202 of roughly 80 ms. Correlation between the return echo signals at the higher PRF enables the shear wave to be tracked and its speed in the tissue determined. As will be appreciated by those skilled in the art, the shear wave speed is related to the Young's modulus of the tissue (i.e. its stiffness). The system then returns to the imaging mode at a time period 204 and new attenuation values are determined from the ultrasound shots used in the imaging mode.

In one embodiment, a user performs a non-invasive assessment of a patient using a FIBROSCAN® device or similar system in which stiffness and ultrasonic attenuation are being measured. A stiffness measurement is obtained from the median or mean of several measurements for which a transient shear wave is generated. The ultrasonic attenuation is obtained from the ultrasonic signals acquired outside of the time when shear wave measurements are being made. As shown in FIG. 4, the system alternates between a first mode that calculates ultrasound attenuation (period 200) and a second mode that measures tissue stiffness (period 202) by tracking shear waves, until such time as all the required tissue stiffness measurements are obtained.

In some embodiments, and in addition to the ultrasonic signals or echo signals acquired during the imaging modes of time periods 200, 204, . . . (see FIG. 4, showing the imaging mode of time period 200, the imaging mode of time period 204 and imaging modes of subsequent time periods), ultrasonic attenuation can also be calculated using ultrasonic signals acquired during stiffness measurement 202 (and subsequent stiffness measurements). In other words, a combination of ultrasonic signals acquired during the imaging modes of time periods 200, 204, . . . and ultrasonic signals acquired during stiffness measurement of time period 202 and/or of subsequent time periods could be used to determine the CAP value. In this embodiment, the ultrasonic signals acquired during stiffness measurement(s) could also be processed using the above described one or more quality criteria. In other embodiments, not all ultrasonic signals acquired during the imaging modes of time periods 200, 204, . . . outside stiffness measurements are processed to determine the CAP value. This might be the case if the duration of the imaging modes is set to a value longer than 20 seconds. For example, in an embodiment, at least 70% of the ultrasonic signals acquired during the imaging modes of time periods 200, 204, . . . can be processed to determine the CAP value. In another embodiment, at least 80% of the ultrasonic signals acquired during the imaging modes of time periods 200, 204 . . . can be processed to determine the CAP value. In yet another embodiment, at least 90% of the ultrasonic signals acquired during the imaging modes of time periods 200, 204 . . . can be processed to determine the CAP value. In another embodiment, 100% of the ultrasonic signals acquired during the imaging modes of time periods 200, 204, . . . can be processed to determine the CAP value.

In some embodiments, the processor of the elastography system is programmed such that none of the ultrasonic signals acquired during the imaging mode of the first time period 200 that is before the first stiffness measurement 202 are processed to determine the CAP value. Thus, in FIG. 4, ultrasonic signals acquired during the imaging mode of the first time period 200 are not taken into account; rather, the CAP value is determined using ultrasonic signals acquired during the imaging modes of the second time period 204 and subsequent time periods, . . . occurring after the first stiffness measurement of time period 202. Indeed, it might be desirable not to determine, or exclude, attenuation values associated with the imaging mode of the first time period 200 occurring before the first stiffness measurement 202 because it might be possible that the target organ (e.g. liver) might not have been properly located during the imaging mode of the first time period 200. In another embodiment, at least 70% of the ultrasonic signals acquired during the imaging mode of the first time period 200 can be processed to determine the CAP value.

In some embodiments, a VCTE examination protocol requires the user to apply 10 shear waves to the patient and the displayed stiffness is determined from the median of the 10 measurements. In some embodiments, a CAP measurement is obtained from of the attenuation values obtained from all return echo signals occurring during the imaging mode between VCTE measurements. In other embodiments, attenuation values obtained during the course of several imaging time periods are accumulated and used to compute the CAP measurement. For example, if 400 valid attenuation values are suggested for CAP measurements and the PRF is 20 shots/sec, then the time required to accumulate the required number of attenuation values is at least 20 seconds and may be longer than the time of a single imaging period.

Figure 5:
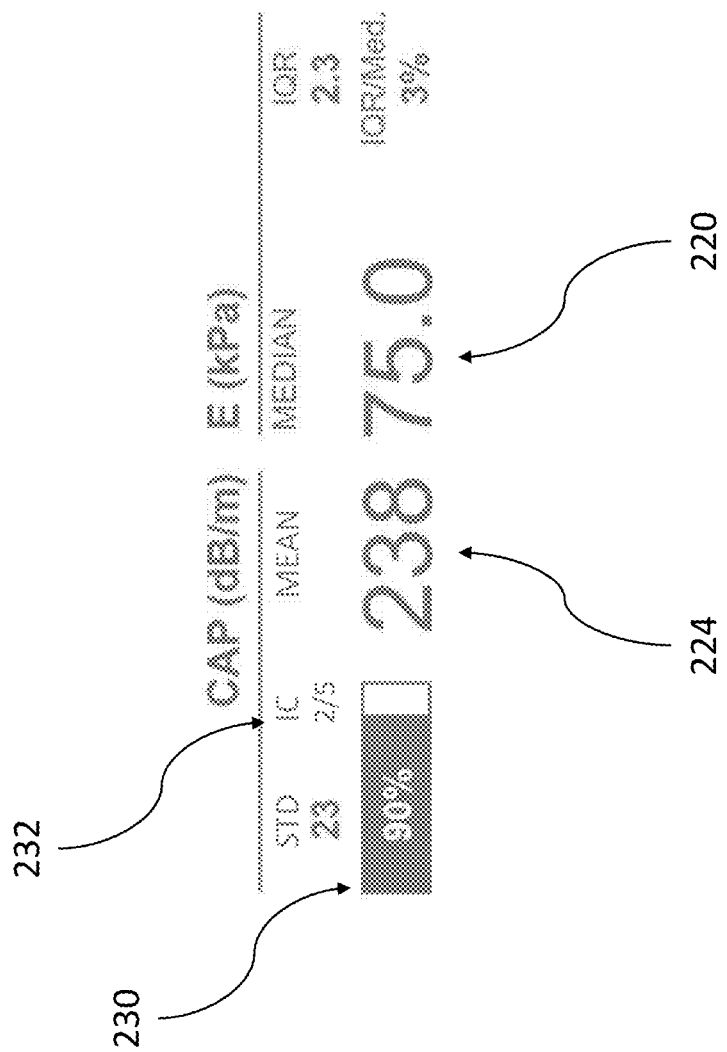
FIG. 5 is a representative display of a CAP measurement produced in accordance with some embodiments of the disclosed technology.

FIG. 5 shows a representative display of a tissue stiffness measurement 220 (E in kilopascal) and ultrasound attenuation 224 (CAP in dB/m), with a standard deviation of 23 dB/m. FIG. 5 also shows quality metrics for the stiffness measurements such as IQR or inter-quartile results or the ratio of IQR/median which are indicative of the confidence that the stiffness measurements is correctly measured. In some embodiments, the display also includes a graph 230 showing the number of "good" attenuation values used to compute the CAP value compared with the suggested minimum number of attenuation values. In the example shown, the bar graph 230 shows 90%, which indicates that only 90% of the minimum number of suggested attenuation measurements were used in computing the CAP value. In some embodiments, the bar graph 230 can be over 100% if more than the required minimum number of attenuation values are accumulated. In some embodiments, the bar graph may display a numeric value ranging from 0 to 10 where 0 means 0% and 10 means 100%. By doing so, the operator may end the exam when 10 is reached, which is consistent with what the operator does for stiffness measurements with the currently available FIBROSCAN® system e.g. the operator stops when 10 valid stiffness measurements are obtained.

In the embodiment shown, the display also includes a quality indicator 232. In this example, the quality indicator 232 shows a number of 2/5 i.e. the CAP measurement displayed has a quality of 2 out of a possible 5. However, other scales could be used. In some embodiments, the quality indicator is computed based on the number of good data obtained compared with the desired number of good data and with the number of Gaussian peaks discovered in the histogram. The particular metrics by which the CAP quality is measured may be determined based on a statistical analysis of the CAP measurements produced and their corresponding histograms versus actual fat content in a subject's liver as determined by MRI studies of subjects. In another embodiment, the display may be configured to display the presence of more than one Gaussian peaks that have an amplitude above a predetermined threshold (e.g. using numerals "1", "2" . . . ), thereby informing the operator of the presence of different zones of fat contents in the patient's liver.

FIG. 6 represents another possible display on a user interface that shows the operator the tissue stiffness value and the CAP measurement for a subject. In the example shown, the display 250 includes a TM-mode image 252 created from received echo signals. A box 254 includes A-line echo data. In one embodiment the A-line echo data is averaged over 0.5 seconds to smooth it out. In some embodiments, the color of the box surrounding the A-line data is indicative of whether the quality criteria of the current ultrasonic line is good or bad. In one embodiment, the box 254 is shown in a green outline 256 when the quality criteria is good.

In the embodiment shown, the display 250 also includes a graphic 258 representing the amount of force applied to the probe tip in contact with the skin of the patient. Some probes include a force sensor that produces a signal that is read by the processor and used to control the graphic 258 to show when the user is applying a force that is in a desired range for tissue measurements. For systems that calculate both tissue stiffness and CAP measurements, the display includes an elastogram (or shear wave propagation map) 260 that shows the slope (e.g. speed) of a shear wave induced in the tissue. The elastogram 260 has a conventional diagonal stripe representing how the shear wave travels through the tissue as a function of depth and time. Finally, the display 250 includes the CAP 262 and tissue stiffness 264 measurements. In some embodiments, quality metrics for the measurements can also be displayed such as IQR or inter-quartile results or STD standard deviation which are indicative of the confidence that the stiffness and CAP measurements are correctly measured.

Figure 7A:
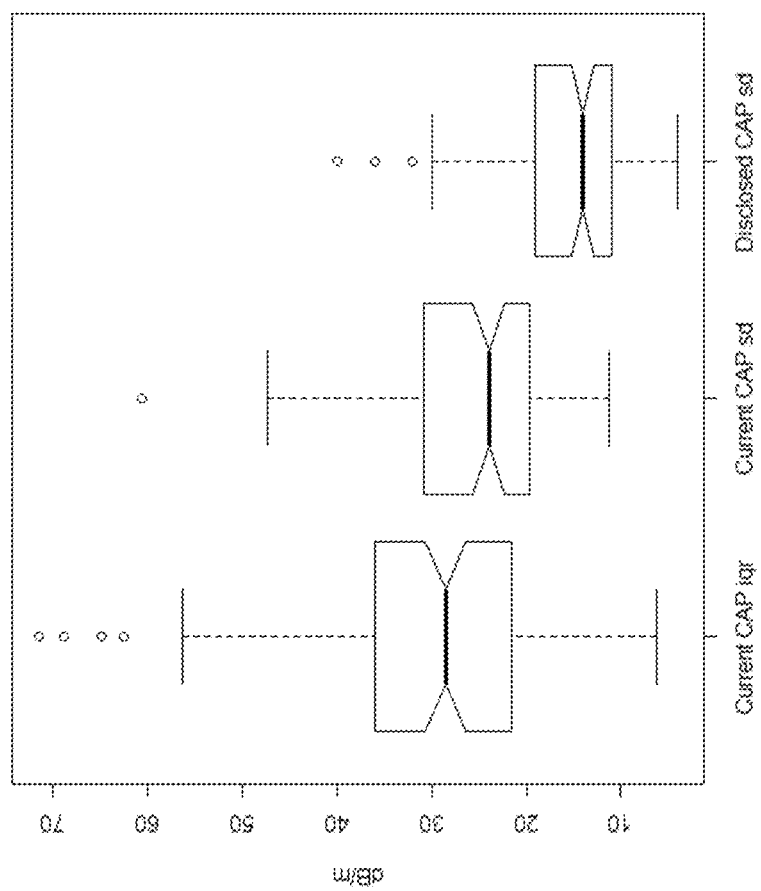
FIGS. 7A-E show the results of conventional CAP and disclosed CAP in a cohort of 113 patients, FIGS. 8A-B schematically illustrate the spatial averaging of the acquired ultrasonic lines obtained according to the conventional method for measuring CAP (FIG. 8A) and according to the method for measuring the disclosed CAP in accordance with the disclosed technology (FIG. 8B)
Figure 7C:
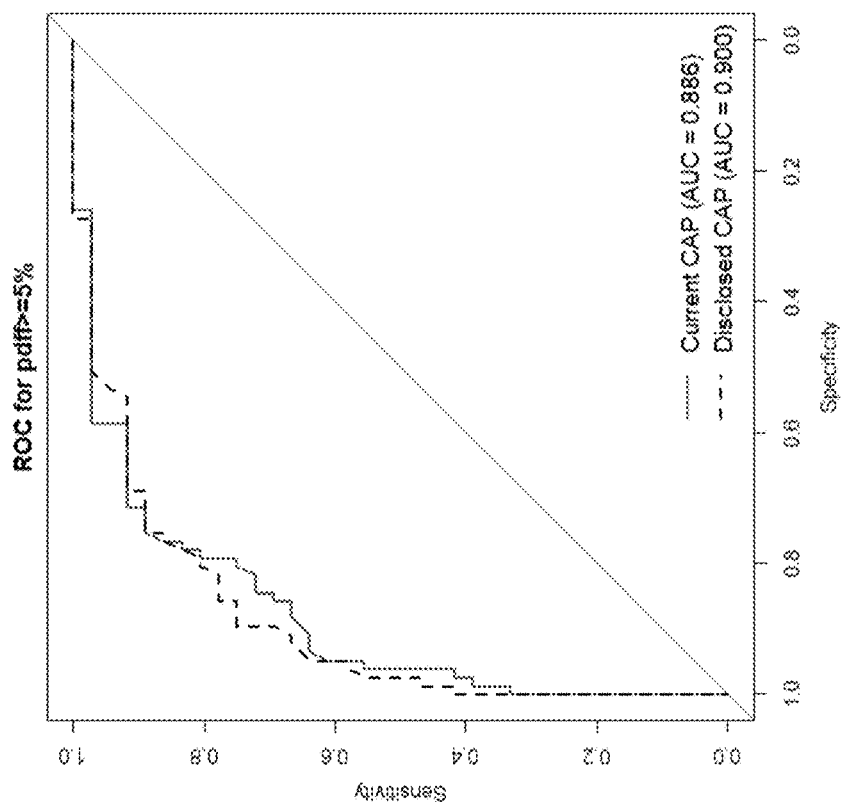
Figure 7B:
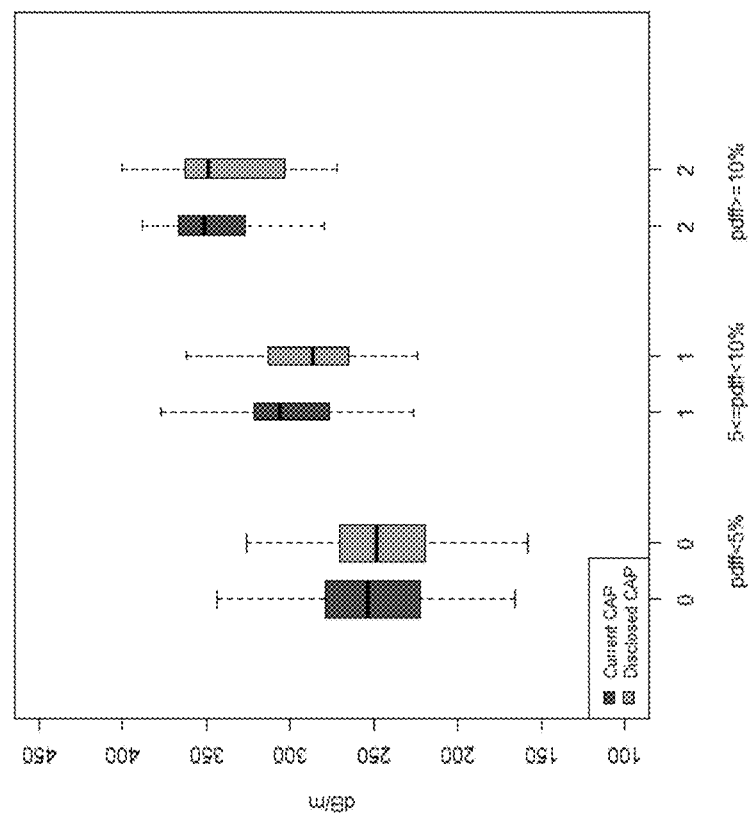
Figure 7D:
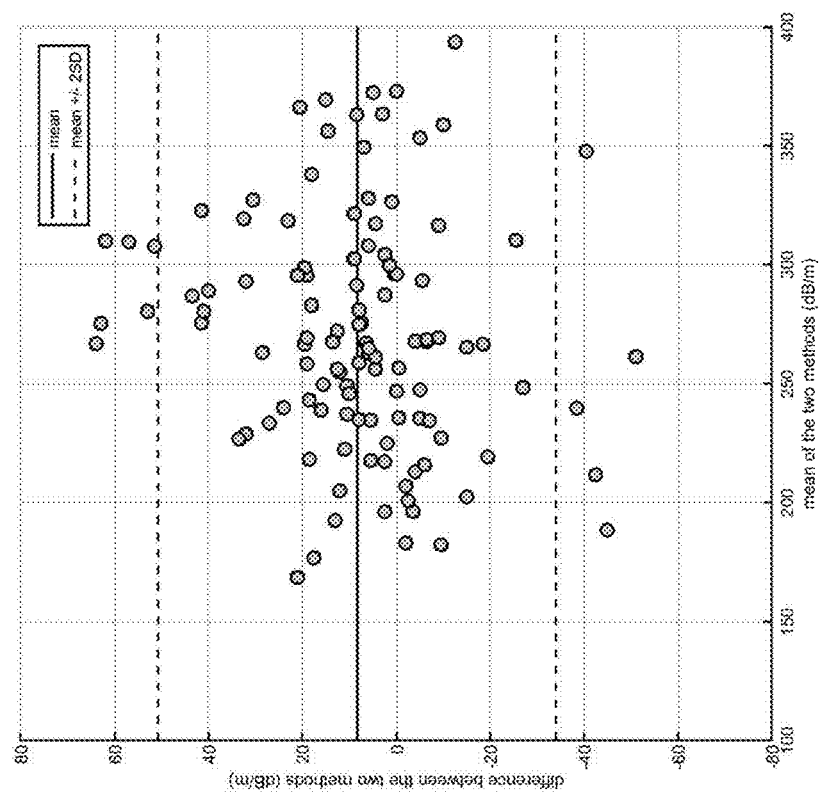
Figure 7E:
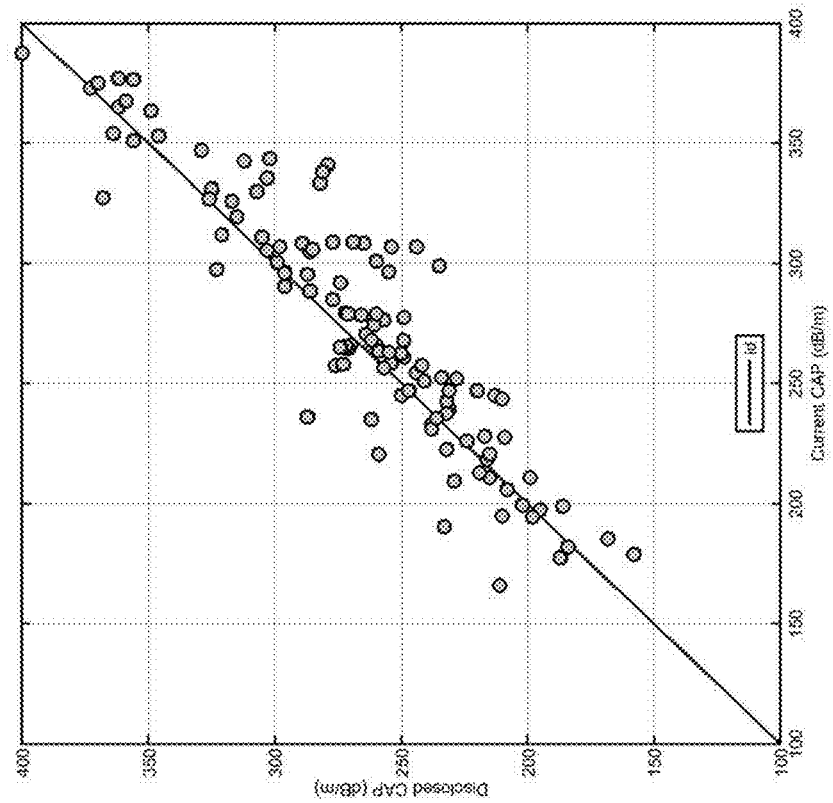

FIGS. 7A-E show the performances of conventional CAP (Current CAP) and disclosed CAP (Disclosed CAP) in a cohort of 113 patients using the same device. The sequence of imaging mode and stiffness measurement mode shown at FIG. 4 was applied to each of the 113 patients. Ten (10) VCTE measurements were conducted for each patient. For each patient, the conventional CAP (Current CAP) was measured with ultrasonic signals acquired during stiffness measurement (i.e. mode 202 in FIG. 4), which corresponds to the conventional method for determining CAP. The disclosed CAP (Disclosed CAP) was measured with ultrasonic signals acquired exclusively during the imaging mode 200, 204 shown in FIG. 4, in accordance with the disclosed technology. The patients were measured with both methods and the CAP results were compared to a reference method that assesses steatosis. The steatosis can be assessed by a pathologist according to histological scoring systems. As known in the art, steatosis is defined according to the number of hepatocytes with fatty accumulation: S0 (<5 or 10% depending on the trial), S1 (5 or 10-33%), S2 (34-66%), S3 (>66%). See the publications "The controlled attenuation parameter (CAP): A novel tool for the non-invasive evaluation of steatosis using Fibroscan®" by M. Sasso et al., published in Clinical Research in Hepatology and Gastroenterology, 2012; "Controlled Attenuation Parameter (CAP): A Novel VCTE™ Guided Ultrasonic Attenuation Measurement for the Evaluation of Hepatic Steatosis: Preliminary Study and Validation in a Cohort of Patients with Chronic Liver Disease from Various Causes" by M. Sasso et al., published in Ultrasound in Medicine and Biology, 2010. As liver biopsy is an invasive procedure, MRI-PDFF was used as the reference method for the measurement of liver fat. This method is well known in the art. FIG. 7A shows a comparison of the variabilities of each method. Conventional CAP variability (Current CAP) is assessed with both by InterQuartile Range (IQR) and standard deviation (sd). As can be seen in FIG. 7A, the variability of disclosed CAP is much better than the variability of conventional CAP. In other words, the CAP values obtained according to the disclosed technology are better to monitor the progression or regression of a disease. As a result, the described technology significantly improves the diagnostic of steatosis in a patient's liver. FIG. 7B shows the dispersion of CAP measurements in 3 patient groups for both methods. The groups correspond to increasing liver fat content (pdff<5%, 5<=pdff<10% and pdff>=10%). The width of each box is representative of the number of patients belonging to each group (i.e. pdff<5%, 5<=pdff<10% and pdff>=10%). As can be seen in FIG. 7B, the CAP values measured according the conventional method and the method according to the disclosed technology increase with the liver fat content, which corresponds to an increase of pdff percentage. Thus, a good correlation exists between the CAP values and the measurements of liver fat content. FIG. 7C shows the area under the ROC curve (AUROC) for the diagnosis of liver steatosis of more than 5% using MRI-PDFF as a reference. The performance of the disclosed CAP (AUROC=0.900) is better than the conventional CAP (AUROC=0.886) in terms of AUROC. In other words, the CAP values obtained according to the disclosed technology provide a steatosis diagnostic that is closer to the one obtained by the pathologist than the current CAP: the clinical performance of the disclosed method for measuring the disclosed CAP is better than that of the conventional method. This improvement is attributed to the decrease of variability of the disclosed CAP. FIG. 7D shows a Bland-Altman plot comparing the two methods. The bias between conventional and disclosed CAP methods is very low: −1.3 dB/m which indicates that the two method are equivalent. FIG. 7E shows a scatter plot of the CAP values obtained with the conventional method and the method of the disclosed technology for the 113 patients. As can be seen in FIG. 7E, statistically, a very good correlation is found between the conventional method for measuring the current CAP and the method according to the disclosed technology for measuring the disclosed CAP. Thus, the mean values for the disclosed CAP and the mean values of the current CAP are the same. However, the variability of the disclosed CAP and the variability of the current CAP are different.

FIGS. 8A-B schematically illustrate the spatial averaging of the acquired ultrasonic lines obtained according to the conventional method for measuring CAP (FIG. 8A) and according to the method for measuring the disclosed CAP in accordance with the disclosed technology (FIG. 8B). FIGS. 8A-B illustrate a probe that emits ultrasonic signals and that receives ultrasonic echoes. The probe may be the probe of the FIBROSCAN® system. The probe is applied against the skin of the patient. FIGS. 8A-B also show the various positions of the target organ (e.g. liver) during acquisition of the ultrasonic lines or echo signals. The displacement of an organ such as liver is typically of several centimeters due to respiratory motion. Liver motion speed due to respiration is typically of the order 1 centimeter per second.

In FIG. 8A, ultrasonic lines or echo signals are acquired during stiffness measurement. As explained above, during a single stiffness measurement, ultrasound lines or echo signals are acquired at a high frame rate of 6000 shots/s for a period of 80 ms. Because the organ (e.g. liver) moves during measurement, the measurements of stiffness are done at different locations in the organ. This is shown in FIG. 8A, where each line schematically represents a stiffness measurement, which corresponds to 80 ms of acquisition of ultrasonic lines or echo signals. The CAP measured according to the conventional technology is done with echo signals captured from only the different locations illustrated in FIG. 8A, which results in poor spatial averaging of the acquired signals.

By contrast, in FIG. 8B, the ultrasound shots are emitted with a rate of repetition of less than 50 Hz and for example equal to 20+/−5 Hz. As indicated above, this low rate of repetition allows recording of the reflected ultrasound signals that are decorrelated with one another due to the difference in time of acquisition compared to the respiratory motion speed. With a repetition frequency of 20 Hz, ultrasound signals are acquired every 50 ms. The respiratory frequency is typically between 12-50 cycles per minute which translates to 1.2-5.0 seconds. In 50 ms, the displacement would be of 2 mm which is enough to decorrelate the ultrasound signal. Using decorrelated ultrasound signals improves the reliability of the measurements while reducing measuring errors. Furthermore, because a high number of ultrasonic lines (echo signals) are acquired over a long period of time (at least 5 seconds, typically 20 seconds), echo signals or ultrasonic lines are collected from a larger area than that shown in FIG. 8A, which significantly improves the spatial averaging of the acquired ultrasonic lines.

Figure 9:
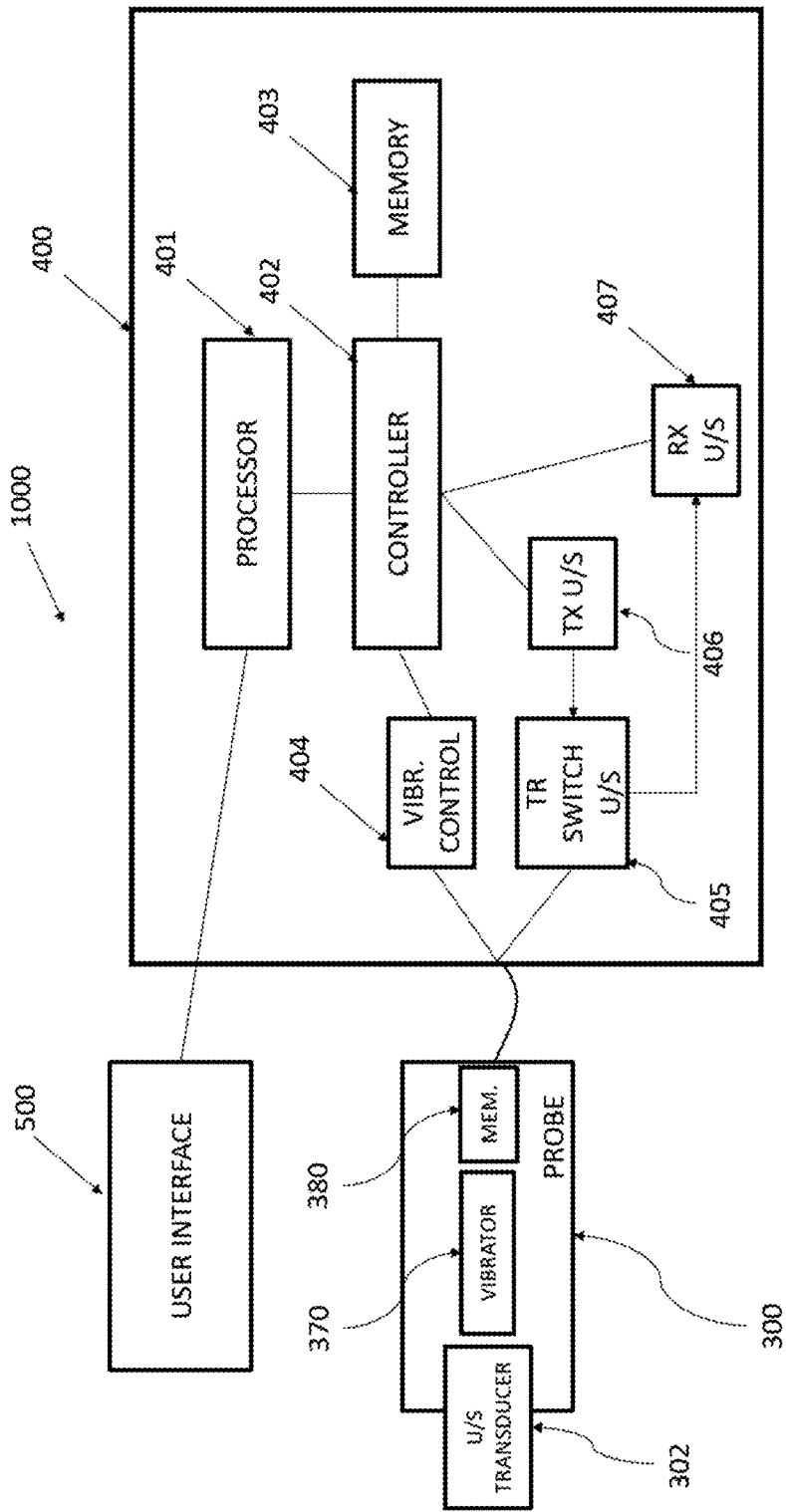
FIG. 9 is a block diagram of a system for producing CAP measurements in accordance with some embodiments of the disclosed technology.

FIG. 9 is a block diagram of an elastography system 1000 for computing CAP measurements from ultrasound data in accordance with some embodiments of the disclosed technology. The elastography system 1000 generally includes a probe 300, a main module 400 and a user interface 500. In some embodiments, the probe 300 is used to detect the shear wave speed and to transmit and receive the ultrasound to acquire the ultrasound attenuation values for computing the CAP measurements. The probe 300 includes an ultrasound transducer 302, a vibrator 370 and a memory 380. The ultrasound transducer 302 in the probe tip is for example a single element transducer but could also be a 1, 1.5 or 2-dimensional array. The main module 400 includes a processor 401, a controller 402, a memory 403, a vibration controller 404, a switch 405 for alternatively transmitting and receiving ultrasonic signals, an ultrasonic transmitter module 406 and an ultrasonic receiver module 407. The processor 401 is configured to execute machine executable instructions stored in the memory 403 for instructing the controller 402 to control the vibration controller 404 for emitting a shear wave during stiffness measurement, to control the ultrasonic transmitter module 406 for emitting ultrasonic signals and to control the ultrasonic receiver module 407 for receiving the echo signals during operation of the system 1000. Ultrasound signals received by the transducer 302 are processed by the ultrasonic receiver module 407 where they are filtered, digitized and stored in the memory 403. The ultrasonic transmitter module 406 is used to deliver the ultrasound shots to the tissue for imaging and for collecting the attenuation data. The programmed processor 401 analyzes the received signals to compute the CAP measurements from histogram of ultrasound attenuation data. Modules 401, 402, 404, 405, 406 and 406 can be in the form of different circuitries.

If the same probe is used for elastography, the probe 300 also includes an electromagnetic actuator 370 (vibrator) similar to an acoustic speaker with a voice coil coupled to the probe tip to generate a physical movement of the tip of the transducer in order to produce the shear wave in the tissue. In the embodiment shown in FIG. 9, the probe is used for both VCTE and CAP measurements. However, in some embodiments, the probe can be configured to only transmit and receive ultrasound signals for use in computing CAP measurements. In this case, the probe may not include an electromagnetic actuator.

In another embodiment, the ultrasound system may be a system configured to carry out CAP measurements without being configured to carry out VCTE measurements. The ultrasound system of this embodiment is similar to the one of FIG. 9 but lacks the vibrator 370 and the vibration controller 404. In this embodiment, the ultrasound system may include a probe having an ultrasound transducer, a main module and a user interface. Like in FIG. 9, the main module may include a processor, a controller, a memory, a switch for alternatively transmitting and receiving ultrasonic signals, an ultrasonic transmitter module and an ultrasonic receiver module. The processor is configured to execute machine executable instructions stored in the memory for instructing the controller to control the ultrasonic transmitter module for emitting ultrasonic signals and to control the ultrasonic receiver module for receiving the echo signals during operation of the system. Ultrasound signals received by the transducer are processed by the ultrasonic receiver module where they are filtered, digitized and stored in the memory.

The ultrasonic transmitter module is used to deliver the ultrasound shots to the tissue and to collect the attenuation data. The programmed processor analyzes the received signals to compute the CAP measurements from histogram of ultrasound attenuation data. The machine executable instructions stored in the memory are specifically designed to control the ultrasonic transmitter module for emitting ultrasonic signals at a rate of repetition of less than 100 Hz, for example 50 Hz in an embodiment, and for example equal to 20+/−5 Hz. As indicated above, this low rate of repetition allows recording of the reflected ultrasound signals that are decorrelated with one another due to the difference in time of acquisition compared to the respiratory motion speed. Furthermore, the machine executable instructions stored in the memory are specifically designed to control the ultrasonic receiver module to acquire echo signals or received ultrasonic lines for a period of time that is much longer than that used during stiffness measurements (i.e. about 80 ms). This improves spatial averaging of the acquired data. In an embodiment, the period of time is set to at least 5 seconds, and in an embodiment at least 10 seconds, and in another embodiment at least 20 seconds. For example, in an embodiment, a CAP measurement may be carried out using echo signals acquired over a period of time that is at least 30 seconds, or at least 45 seconds, or at least 1 mn and at most one or several minutes, for example at most 5 minutes, for example at most 4 minutes, for example at most 3 minutes, for example at most 2 minutes, for example at most 1 minute.

As described, it can be seen that the ultrasound system of the disclosed technology is adapted to collect attenuation data used to compute CAP measurements as it is imaging the tissue before allowing a user to perform a VCTE examination. Received ultrasound data and attenuation measurements are subjected to one or more quality tests before being included in the group of measurements used to compute a CAP value.

According to one implementation, the step of calculation CALC is performed using a histogram representing the valid accumulated ultrasonic attenuation values. In this case the histogram is automatically adjusted using one or more bell-shaped curves.

According to one implementation, the adjustment is made using mathematical functions of the Gaussian type. In other words, the step of calculation includes a step of detection of one or more Gaussian curves forming the histogram of valid accumulated values. The center of each Gaussian curve then corresponds to a value representative of the ultrasound parameter of the viscoelastic medium to be characterized.

Beneficially, automatic detection of several bell-shaped curves comprising the histogram enables different regions of the viscoelastic medium to be detected. In other words, the method according to the disclosed technology enables regions of the viscoelastic medium with different properties to be identified.

In some embodiments, the method according to the disclosed technology also includes a step of displaying one or more values representative of the ultrasound parameter. In some embodiments, the step of displaying is implemented only if the number of valid accumulated ultrasonic attenuation values is higher than a predetermined minimum threshold.

Beneficially, using a high number of valid accumulated ultrasonic attenuation values enables a statistical analysis of the data to be performed, and the risk of systematic error in measuring the ultrasound parameter to be minimized.

According to one implementation, if several Gaussian curves are detected, only the most representative value is displayed. In this case, the most representative value is automatically chosen by the method, for example on the basis of the properties of the various detected Gaussian curves.

According to one implementation, the most representative value corresponds to the region of the viscoelastic medium which has been insonified for the longest time during the examination. In an embodiment, this value may be obtained in real time, i.e. as the operator operates the disclosed system in the first/imaging mode. Alternatively, this value may be obtained when the operator stops the exam. In yet another embodiment, the value is obtained when the exam stops automatically.

According to one implementation, the measuring error associated with the value representing the ultrasound parameter is determined from the standard deviation of the Gaussian fitted to the histogram of the ultrasonic attenuation values.

It is important to note that if the value of the ultrasound parameter is calculated from a small number of ultrasonic attenuation values, the accuracy of the calculation is reduced. In this case, the valid accumulated attenuation values are distributed along an asymmetrical curve with greater uncertainty concerning the average value.

According to one implementation, the predetermined minimum threshold of valid accumulated ultrasonic attenuation values is equal to 400 valid ultrasound shots.

The calculated value of the ultrasonic attenuation parameter, and the measuring error associated with this value, can be communicated to the operator during the displaying step. For example, these values are displayed on a screen or an indicator.

Beneficially, the operator checks in real time the changes in the numbers of valid ultrasound shots, and can, if necessary, correct the positioning of the probe to reduce the duration of the examination, or to improve its quality.

According to one implementation, method according to the disclosed technology also includes a step of determining the measuring depth of the ultrasound parameter.

According to one implementation, the measuring depth is determined prior to step of emitting ultrasound in a sequence of ultrasound shots. In this case the operator can implement pre-location of the region of interest. According to one implementation, the measuring depth is kept constant for the entire duration of the measurement of the ultrasound parameter.

According to one implementation, the ultrasonic attenuation values are measured and accumulated for more than one, such as three, different ranges of depths. The three ranges of depths can be staggered amounts such as by 5 mm or ¼ inch. In this case, only the gauge representing the valid accumulated attenuation values is displayed. At the end of the examination, the operator chooses the range of depth to be used. For example, the depth range may depend on the distance between the ultrasound probe and the outer wall of the medium to be characterized. For example, if the medium to be characterized is a human or animal liver, the range of depth to be used is chosen on the basis of the distance between the ultrasound probe and the capsule of the liver.

According to one implementation, a method according to the disclosed technology includes a step of display of the measuring depth. The measuring depth and of the number of valid ultrasound signals can be displayed simultaneously.

Alternatively, the ultrasound parameter can be measured in three different ranges of depths. At the end of the examination a single depth will be used based on the distance between the ultrasound probe and the outer wall of the viscoelastic medium to be characterized.

During the calculation step, the histogram is adjusted using a Gaussian curve, which enables a value representative of the ultrasound parameter to be calculated. The Gaussian curve is automatically detected in order to adjust the histogram. The center of the Gaussian curve and its standard deviation correspond respectively to the value representative of the ultrasonic attenuation and the associated measuring error.

Beneficially, the results of calculation step are displayed only if the number of valid accumulated ultrasonic attenuation values is higher than a predetermined minimum threshold. According to one implementation, the minimum number of valid accumulated ultrasonic attenuation values is 400.

According to one implementation, the exam stops automatically when the number of valid accumulated ultrasonic attenuation values reaches a predetermined threshold, for example 400.

According to one implementation, the number of valid accumulated ultrasonic attenuation values is represented in real time by an indicator. The results of the adjustment of the histogram are displayed only if the number of valid accumulated ultrasonic attenuation values is higher than minimum threshold.

According to one implementation, the gauge can also display a recommended threshold for the valid ultrasonic attenuation values.

As indicated above, in some embodiments the histogram created from the acquired attenuation values includes two or more different peaks corresponding to two or more different regions of the viscoelastic medium.

During step of calculating the CAP measurements, the presence of two regions is detected automatically and the histogram is adjusted, for example using an adapted expectation maximum algorithm on the two Gaussian curves. Each Gaussian curve corresponds to a region of the viscoelastic medium, where the two regions are characterized by two different values of the ultrasound parameter.

Beneficially, method according to the disclosed technology enables a non-uniform viscoelastic medium with several regions to be characterized, where each region is characterized by a given representative ultrasonic attenuation value.

In addition, the method enables the most representative region of a non-uniform viscoelastic medium to be detected automatically and according to a predetermined criterion. For example, the method includes a step of automatically selecting the part of the histogram corresponding to the region that has been swept for the longest time. In this case, the measuring error is calculated as the standard deviation of the values of the Gaussian curve.

Beneficially, method according to the disclosed technology enables the measuring error associated with the value of the ultrasonic attenuation parameter to be reduced, whilst increasing the reliability of the measuring method.

Another aspect of the disclosed technology is a device to implement the method.

According to one implementation, the device according to the invention includes:

an ultrasound probe including an ultrasound transducer for the emission of a sequence of ultrasound shots and for recording of the ultrasound signals reflected by the medium to be characterized;

means, such as a digital signal processor or programmed processor, that is configured for the automatic accumulation of valid attenuation values; and means, such as a digital signal processor or programmed processor, that is configured for the calculation, using the valid accumulated attenuation values, of one or more values representative of the ultrasound parameter of the viscoelastic medium.

The ultrasound probe can include one or more ultrasound transducers. The ultrasound probe allows the emission of the sequence of ultrasound shots.

According to one implementation, the ultrasound probe includes a single ultrasound transducer or single-element ultrasound transducer with a diameter of between 4 and 12 mm.

According to one implementation, the rate of repetition of the ultrasound shots is between 10 Hz and 50 Hz during attenuation value acquisition.

According to one implementation, the center frequency of the ultrasound shots is between 1 MHz and 10 MHz According to one implementation, a display means include a video display with a touchscreen that is designed to receive instructions to modify the parameters or to activate measuring. In other embodiments, the display may be a remote device (laptop, iPad, smart phone) connected to the system by a wired or wireless communication link to display the data produced from the ultrasound shots.

In some embodiments, the value representative of the ultrasound parameter is displayed only if the number of good or valid ultrasonic attenuation values is higher than a predetermined minimum threshold.

According to one implementation, the display means are designed to display an indicator which represents the number of valid ultrasound shots.

According to one implementation, the indicator is produced in the form of a gauge displaying in real time the number of valid ultrasound shots compared to the predetermined threshold.

According to one implementation, the indicator in the form of a gauge displays a recommended threshold of valid ultrasonic attenuation values.

According to one implementation, the ultrasound probe is a probe for transient elastography.

A processor is programmed or configured to analyze the histogram of accumulated values and a parameter is estimated only if the analyzed signals are decorrelated with one another to increase the reliability of the measurement. Using automatic analysis of the high number of good ultrasonic echo signals, the method according to the technology also enables a region to be selected that is representative of the viscoelastic medium to be characterized.

In some embodiments, a first aspect of the disclosed technology is a method for measuring an ultrasound parameter of a viscoelastic medium to be characterized including the following steps:

emitting a sequence of ultrasound shots using an ultrasound transducer and recording the ultrasound signals reflected by the medium to be characterized;

automatically accumulating valid ultrasonic attenuation values, where the valid ultrasonic attenuation values are obtained from the recorded reflected ultrasound signals; and using the valid accumulated ultrasonic attenuation values, calculating one or more values representative of the ultrasound parameter of the viscoelastic medium.

The expression "ultrasound shot" is understood to mean the emission of an ultrasound pulse in the medium to be characterized. According to one implementation, the viscoelastic medium to be characterized is a human or animal liver.

The expression "recording of reflected ultrasound signals" is understood to mean the recording on-the-fly of the echoes generated by the reflecting particles present in a defined range of depths of the analyzed medium.

An example of an ultrasound parameter measured by the method according to the invention is an ultrasonic attenuation parameter.

The expression "ultrasonic attenuation" is understood to mean any parameter that reflects the ultrasonic attenuation: Broadband Ultrasound Attenuation (BUA, in dB/cm/MHz), attenuation measured at a particular frequency (in dB/cm), Controlled Attenuation Parameter (CAP), etc.

The expression "valid ultrasonic attenuation value" is understood to mean an ultrasonic attenuation value with a good quality criteria. An example of a non-valid ultrasonic attenuation value is a negative ultrasonic attenuation value or an attenuation value that is out of an expected range. An example of a non-valid ultrasonic attenuation value is an ultrasonic attenuation value obtained from an ultrasound signal which exhibits features from vessels. For example, a criterion of validity of an ultrasound signal is given by the tool "Liver Targeting Tool", or LTT, developed by the applicant (also see the document "Influence of heterogeneities on ultrasound attenuation for liver steatosis evaluation (CAP™): relevance of a liver guidance tool Ultrasonics Symposium (IUS), 2013 IEEE International".

With some embodiments, the expression "accumulating valid ultrasonic attenuation values" is understood to mean the recording of valid ultrasonic attenuation values. According to one implementation, the accumulation of these values is represented by a histogram of valid ultrasonic attenuation values.

With some embodiments, the expression "value representative of the ultrasound parameter" is understood to mean a value representative of the insonified viscoelastic medium.

For example, if the ultrasound parameter measured by the method is an ultrasonic attenuation parameter, the representative value is a value of the ultrasonic attenuation parameter calculated using the valid accumulated ultrasonic attenuation values. According to one implementation, the value most representative of the ultrasound parameter is the value associated with the region of the medium which has been insonified for the longest time during the examination, or with the region for which the number of valid attenuation values is the highest. Alternatively, the value most representative of the ultrasound parameter is the value associated with the region of the medium for which the greatest number of good attenuation values has been recorded.

According to one implementation, the method according to the technology includes a step of displaying one or more values representative of the ultrasonic attenuation parameter, where the display is made only if the number of valid accumulated ultrasonic attenuation values is higher than a predetermined minimum threshold. For example, the value of the ultrasonic attenuation parameter is displayed only if the number of valid recorded ultrasound signals is higher than 100, for example higher than 200, such as 400 or more.

According to one implementation, the ultrasound shots are emitted with a rate of repetition of less than 50 Hz and for example than or equal to 20+/−5 Hz. When the viscoelastic medium is a human or animal organ, the difference between the respiratory frequency and the rate of repetition of the ultrasound shots enables ultrasound signals which are decorrelated in relation to one another to be recorded.

Beneficially, having a high number of valid attenuation values which are decorrelated in relation to one another improves the likelihood that these values are representative of the insonified medium.

Beneficially, the statistical analysis of the accumulated valid ultrasonic attenuation values enables the reliability and reproducibility of the method of measuring the ultrasound parameter to be improved.

According to one implementation, the step of calculation of one or more values representative of the ultrasound parameter of the viscoelastic medium is made using the histogram representing the valid accumulated ultrasonic attenuation values.

Due to the fact that there is a high number of ultrasonic attenuation values that are decorrelated in relation to one another, the histogram can be described by one or more bell-shaped curves, such as Gaussian curves.

According to one implementation, it is possible to adjust the histogram of the valid accumulated ultrasonic attenuation values using one or more mathematical functions of the Gaussian type. In this case, the maximum of each Gaussian curve corresponds to an attenuation value representative of a region of the insonified viscoelastic medium.

According to one implementation, the measuring error associated with the value representing the ultrasonic attenuation parameter is calculated as the standard deviation of the Gaussian fitted to the valid ultrasonic attenuation values.

Beneficially, due to the high number of values, the statistical representativeness of the standard deviation is significant, and enables the measuring error associated with the value of the ultrasound parameter to be estimated correctly.

Beneficially, the method according to the disclosed technology enables the presence of different regions within the viscoelastic medium to be detected automatically, where each region corresponds to a bell-shaped curve describing a portion of the histogram of the valid accumulated ultrasonic attenuation values. In other words, a histogram described by a single bell-shaped curve corresponds to a completely uniform medium.

Beneficially, the method according to the disclosed technology enables several values of the ultrasonic attenuation parameter to be measured, where each value is representative of a different area of the insonified medium. In other words, the method according to the technology enables an area characterized by a value of the ultrasound parameter, relative to an area characterized by a different value of the ultrasound parameter, to be selected.

According to one implementation, when the histogram representing the valid accumulated ultrasonic attenuation values is described by several bell-shaped curves corresponding to different regions, the method according to the invention also includes a step of automatically choosing the value of the ultrasound parameter most representative of the insonified medium. The ultrasound parameter measuring method according to the technology may also have one or more of the characteristics below, considered individually, or in all technically possible combinations:

The method according to the disclosed technology also includes a step of displaying one or more values representative of the ultrasound parameter of the viscoelastic medium, where the step of display is implemented only if the number of valid accumulated ultrasonic attenuation values is higher than a predetermined minimum threshold.

In some embodiments, the method according to the technology also includes a step of displaying a gauge indicating the number of valid accumulated ultrasonic attenuation values (or a similar number). The gauge includes an indicator of the predetermined minimum threshold of valid accumulated values and/or an indicator of a predetermined recommended threshold of valid accumulated values. In some embodiments, one or more values representative of the ultrasound parameter are calculated from a histogram representing the valid accumulated ultrasonic attenuation values. In some embodiments, one or more values representative of the ultrasound parameter are calculated and an automatic adjustment is made using the histogram representing the valid accumulated ultrasonic attenuation values. The automatic adjustment is made using one or more mathematical functions of the Gaussian type. In some embodiments, the ultrasound parameter is an ultrasonic attenuation parameter.

In some embodiments, the ultrasonic attenuation parameter is calculated at several different depths, and the method according to the technology includes a step of choosing a depth (or allowing a user to choose a depth) which is most representative of the medium to be characterized. In some embodiments, the method also includes a step of displaying the measuring depth of the ultrasound parameter. The sequence of ultrasound shots is emitted with an emission rate lower than 50 Hz, and for example lower than or equal to 20+/−5 Hz.

Embodiments of the subject matter and the operations described in this specification (e.g. the elements of block 400 of FIG. 9) can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "programmed processor" encompasses all kinds of apparatus, devices, and machines for processing data, including by way of example a programmable processor, digital signal processor (DSP), a computer, a system on a chip, or multiple ones, or combinations, of the foregoing. The apparatus can include special purpose logic circuitry, e.g., an FPGA (field programmable gate array) or an ASIC (application-specific integrated circuit).

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode), or OLED (organic light emitting diode) monitor, for displaying information to the user and a keyboard and a pointing device, e.g., a mouse or a trackball, by which the user can provide input to the computer. In some implementations, a touch screen can be used to display information and to receive input from a user. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

From the foregoing, it will be appreciated that specific embodiments of the invention have been described herein for purposes of illustration, but that various modifications may be made without deviating from the scope of the invention. Accordingly, the invention is not limited except as by the appended claims.

The invention claimed is:

1. Method for measuring an ultrasound parameter of a viscoelastic medium to be characterized with an elastography system configured to generate a shear wave in a region of interest, the elastography system including an ultrasound transducer configured to emit a sequence of ultrasound shots and to receive corresponding echo signals from the region of interest, and a processor programmed to alternately operate at least in a first mode and a second mode, wherein in the first mode, the processor is programmed to generate a first sequence of ultrasound shots with said ultrasound transducer to measure an attenuation of ultrasound signals in a tissue; and wherein in the second mode, the processor is programmed to control the elastography system to create a shear wave in the tissue; and to generate a second sequence of ultrasound shots with said ultrasound transducer to track how the tissue in the region of interest is moved by the shear wave, the method comprising:

operating the processor in the first mode, said operating comprising generating the first sequence of ultrasound shots with said ultrasound transducer to the region of interest and receiving corresponding first mode echo signals from the region of interest without generating the shear wave which is used to measure shear wave speed in the tissue;

recording first mode ultrasound attenuation values associated with the received first mode echo signals obtained without generating said shear wave, and calculating a value of the ultrasound parameter using at least the first mode ultrasound attenuation values, wherein the first sequence of ultrasound shots has a duration that is longer than the second sequence of ultrasound shots, wherein the method further comprises processing the first mode ultrasound attenuation values using one or more quality criteria to determine, among the recorded first mode ultrasound attenuation values, ultrasound attenuation values that have a predetermined quality level, and wherein the value of the ultrasound parameter is calculated using first mode ultrasound attenuation values that have the predetermined quality level, and wherein the one or more quality criteria include a correlation criterion and wherein the processing includes associating each one of the received first mode echo signals with a correlation coefficient and selecting each of the received first mode echo signal having the correlation coefficient past a predetermined threshold value to determine, among the received first mode echo signals, first mode echo signals that are sufficiently decorrelated.

2. The method of claim 1, wherein the correlation coefficient is calculated based on said one of the received first mode echo signals and previously received first mode echo signals.

3. The method of claim 1, wherein the one or more quality criteria include an attenuation criterion that is defined by a predetermined range of ultrasound attenuation values and wherein the processing includes selecting each of the first mode ultrasound attenuation values that are within the predetermined range.

4. The method of claim 3, wherein the predetermined range is 100-500 db/m.

5. The method of claim 1, wherein the one or more quality criteria include a coupling criterion representative of a coupling force between the ultrasound transducer and a skin of a patient for whom the viscoelastic medium is to be characterized, the coupling criterion defined by a predetermined range of coupling coefficient values, and wherein the processing includes associating each of the received first mode echo signals to a coupling coefficient and selecting each first mode echo signal having the coupling coefficient past a predetermined threshold value.

6. The method of claim 1, wherein the one or more quality criteria include a coefficient of determination of a linear regression applied to the received first mode echo signals.

7. The method of claim 1, wherein the ultrasound parameter is controlled attenuation parameter (CAP).

8. The method of claim 1, further comprising accumulating the ultrasound attenuation values that have a predetermined quality level, wherein the value of the ultrasound parameter is calculated only when a number of the ultrasound attenuation values that have a predetermined quality level reaches a predetermined threshold.

9. The method of claim 1, wherein the value of the ultrasound parameter is calculated only with the first ultrasound attenuation values that are obtained when the processor operates in the first mode.

10. The method of claim 1, further comprising when the processor operates in the second mode, recording second mode ultrasound attenuation values associated with received second mode echo signals;

processing the second ultrasound attenuation values using the one or more quality criteria to determine, among the recorded second mode ultrasound attenuation values, the ultrasound attenuation values that have the predetermined quality level, and calculating the value of the ultrasound parameter using the ultrasound attenuation values that have the predetermined quality level and are obtained with both the first and second mode ultrasound attenuation values.

11. The method of claim 1, further comprising displaying the value of the ultrasound parameter.

12. The method of claim 1, wherein the first sequence of ultrasound shots are transmitted at a pulse repetition rate of under 500 pulses/second.

13. The method of claim 12, wherein the first sequence of ultrasound shots are transmitted at a pulse repetition rate of under 100 pulses/second.

14. The method of claim 13, wherein the first sequence of ultrasound shots are transmitted at a pulse repetition rate between 15 and 25 pulses/second.

15. Method for measuring an ultrasound parameter of a viscoelastic medium to be characterized with an ultrasound system including an ultrasound transducer configured to emit a sequence of ultrasound shots and to receive corresponding echo signals from a region of interest, and a processor programmed to generate, in a first mode, a first sequence of ultrasound shots with said ultrasound transducer to measure an attenuation of ultrasound signals in a tissue, the method comprising:

generating the first sequence of ultrasound shots with said ultrasound transducer to the region of interest and receiving corresponding first mode echo signals from the region of interest without generating a shear wave which is used to measure shear wave speed in the tissue, wherein the first sequence of ultrasound shots are generated at a repetition rate of under 100 pulses/second for a period of time of at least 5 seconds;

recording first mode ultrasound attenuation values associated with the received first mode echo signals obtained without generating said shear wave, and calculating a value of the ultrasound parameter using the first mode ultrasound attenuation values wherein the method further comprises processing the first mode ultrasound attenuation values using one or more quality criteria to determine, among the recorded first mode ultrasound attenuation values, ultrasound attenuation values that have a predetermined quality level, and wherein the value of the ultrasound parameter is calculated using first mode ultrasound attenuation values that have the predetermined quality level, and wherein the one or more quality criteria include a correlation criterion and wherein the processing includes associating each one of the received first mode echo signals with a correlation coefficient and selecting each of the received first mode echo signal having the correlation coefficient past a predetermined threshold value to determine, among the received first mode echo signals, first mode echo signals that are sufficiently decorrelated.

16. The method of claim 15, wherein the repetition rate is between 15 and 25 pulses/second and the period of time is at least 20 seconds.

17. The method of claim 15, wherein the ultrasound system is an elastography system configured to generate a shear wave in the region of interest, wherein the processor is programmed to alternately operate at least in the first mode and a second mode, wherein in the second mode, the processor is programmed to control the elastography system to create a shear wave in the tissue; and to generate a second sequence of ultrasound shots to track how the tissue in the region of interest is moved by the shear wave.

18. A system for measuring ultrasound attenuation in a region of interest in a tissue sample, comprising:
an ultrasound transducer configured to emit a sequence of ultrasound shots and to receive corresponding echo signals from a region of interest; and
a processor that is programmed to alternately operate in a first mode and a second mode, wherein in the first mode, the processor is programmed to
generate a first sequence of ultrasound shots with said ultrasound transducer to measure an attenuation of ultrasound signals in the tissue; and
in the second mode, the processor is programmed to
generate a second sequence of ultrasound shots with said ultrasound transducer to track how the tissue in the region of interest is moved by a shear wave;
wherein the first sequence of ultrasound shots to measure the attenuation of ultrasound signals are transmitted outside of a time period when the processor is operating in the second mode, and
wherein the first sequence of ultrasound shots has a duration that is longer than the second sequence of ultrasound shots and the first sequence of ultrasound shots are generated to the region of interest and corresponding first mode echo signals are received from the region of interest without generating the shear wave which is used to measure shear wave speed in the tissue,
wherein the processor is configured to process the first mode ultrasound attenuation values using one or more quality criteria to determine, among the recorded first mode ultrasound attenuation values, ultrasound attenuation values that have a predetermined quality level, and wherein the value of the ultrasound parameter is calculated using first mode ultrasound attenuation values that have the predetermined quality level, and
wherein the one or more quality criteria include a correlation criterion and wherein the processing includes associating each one of the received first mode echo signals with a correlation coefficient and selecting each of the received first mode echo signal having the correlation coefficient past a predetermined threshold value to determine, among the received first mode echo signals, first mode echo signals that are sufficiently decorrelated.

* * * * *